US009844621B2

(12) United States Patent
Rempfer et al.

(10) Patent No.: US 9,844,621 B2
(45) Date of Patent: Dec. 19, 2017

(54) SEPARATION MATERIAL

(75) Inventors: Martin Rempfer, Gomaringen (DE); Wolfgang Freudemann, Hechingen (DE); Cornelia Winz, Rottenburg-Weiler (DE); Ralf Flieg, Rangendingen (DE); Markus Storr, Filderstadt (DE); Sandra Homeyer, Ofterdingen (DE); Torsten Knoer, Burladingen (DE)

(73) Assignee: GAMBRO LUNDIA AB, Lund (SE)

( * ) Notice: Subject to any disclaimer, the term of this patent is extended or adjusted under 35 U.S.C. 154(b) by 446 days.

(21) Appl. No.: 14/236,921

(22) PCT Filed: Aug. 7, 2012

(86) PCT No.: PCT/EP2012/065394
§ 371 (c)(1),
(2), (4) Date: Feb. 4, 2014

(87) PCT Pub. No.: WO2013/020967
PCT Pub. Date: Feb. 14, 2013

(65) Prior Publication Data
US 2014/0166580 A1 Jun. 19, 2014

(30) Foreign Application Priority Data
Aug. 8, 2011 (EP) .................................. 11176770

(51) Int. Cl.
| *B01D 24/00* | (2006.01) |
| *B01D 39/00* | (2006.01) |
| *B01D 39/14* | (2006.01) |
| *B01D 63/00* | (2006.01) |
| *B01D 67/00* | (2006.01) |
| *B29C 44/04* | (2006.01) |
| *A61M 1/34* | (2006.01) |
| *B01J 20/26* | (2006.01) |
| *B01J 20/289* | (2006.01) |
| *B01J 20/32* | (2006.01) |

(52) U.S. Cl.
CPC ............... *A61M 1/34* (2013.01); *B01J 20/26* (2013.01); *B01J 20/289* (2013.01); *B01J 20/321* (2013.01); *B01J 20/327* (2013.01); *B01J 20/328* (2013.01); *B01J 20/3212* (2013.01); *B01J 20/3219* (2013.01); *B01J 20/3255* (2013.01); *B01J 20/3274* (2013.01); *B01J 20/3278* (2013.01)

(58) Field of Classification Search
CPC .......... C40B 40/12; C40B 50/18; A61M 1/34; B01J 20/3219; B01J 20/3274; B01J 20/328; B01J 20/28033; B01D 2323/06; B01D 2325/36; B01D 69/08
See application file for complete search history.

(56) References Cited

U.S. PATENT DOCUMENTS

| 3,947,352 A | 3/1976 | Cuatrecasas et al. |
| 4,411,832 A | 10/1983 | Cuatrecasas et al. |
| 5,670,483 A | 9/1997 | Zhang et al. |
| 5,955,343 A | 9/1999 | Holmes et al. |
| 6,548,630 B1 | 4/2003 | Zhang et al. |
| 6,800,481 B1 | 10/2004 | Holmes et al. |
| 7,700,746 B2 | 4/2010 | Nilsson |
| 2003/0220245 A1* | 11/2003 | Hubbell ............... A61K 31/337 525/50 |
| 2005/0181973 A1 | 8/2005 | Genove et al. |
| 2005/0202396 A1* | 9/2005 | Ruhe ........................ B01J 20/26 435/4 |
| 2007/0296105 A1 | 12/2007 | Krause et al. |
| 2010/0331198 A1* | 12/2010 | Wang ..................... C07H 15/04 506/9 |
| 2014/0166580 A1* | 6/2014 | Rempfer .................. B01J 20/26 210/650 |
| 2015/0111194 A1* | 4/2015 | Rempfer .................. B01J 20/26 435/2 |

FOREIGN PATENT DOCUMENTS

| EP | 0305687 | 4/1992 |
| EP | 0844015 | 10/2003 |
| EP | 1518870 | 3/2005 |
| EP | 1165159 | 3/2008 |
| EP | 1875956 | 3/2010 |
| EP | 1875957 | 3/2010 |
| EP | 2281625 | 2/2011 |
| EP | 2113298 | 4/2013 |
| EP | 2228126 | 4/2013 |
| WO | WO01/60477 | 8/2001 |

OTHER PUBLICATIONS

PCT Search Report and Written Opinion for PCT/EP2012/065394, dated Sep. 4, 2012.
Lee, Myung-Ryul, et al., "Fabrication of Chemical Microarrays by Efficient Immobilization of Hydrazide-Linked Substances on Epoxide-Coated Glass Surfaces", 2005, Angew. Chem. Int. Ed., No. 44, pp. 2881-2884.
Parthasarathy, N., et al., "Application of Carbohydrate Microarray Technology for the Detection of Burkholderia Pseudomallei, *Bacillus Anthracis* and *Francisella Tularensis* Antibodies", 2008, Carbohydrate Research, No. 343, pp. 2783-2788.
Monsigney et al., "Colorimetric Determination of Neutral Sugars by a Resorcinol Acid Micromethod," 1988 Analytical Biochemistry 175, 525-530.

* cited by examiner

*Primary Examiner* — Ana Fortuna
(74) *Attorney, Agent, or Firm* — Barnes & Thornburg LLP

(57) ABSTRACT

A separation material includes a matrix that is bound to a saccharide, enabling the separation from a liquid of substances that selectively bind the saccharide. A method for preparing the separation material and a method for separating substances from a liquid that selectively bind a saccharide of the separation material are also described. A device employs the separation material for separating from a liquid substances that selectively bind to the saccharide of the separation material.

19 Claims, 2 Drawing Sheets

SEPARATION MATERIAL

CROSS-REFERENCE TO RELATED APPLICATIONS

Figure 1A:
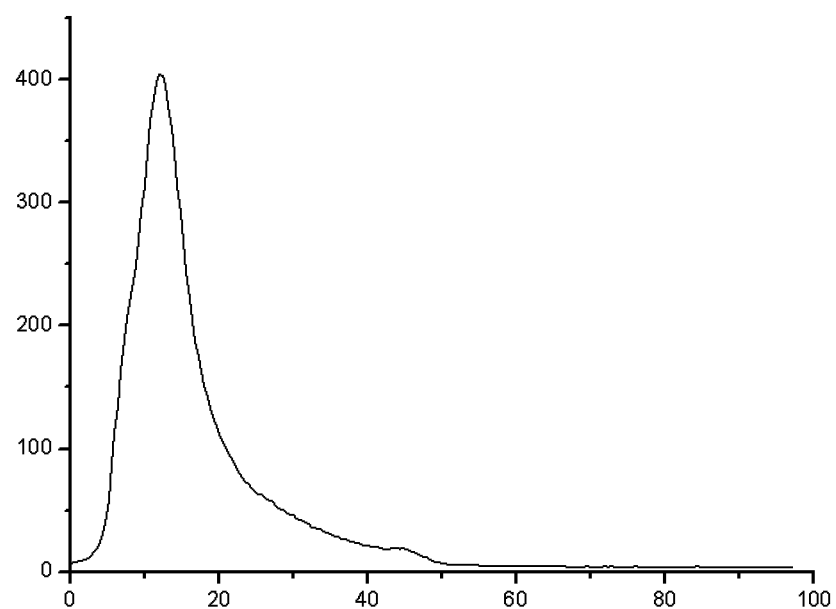

This application is the U.S. national phase of PCT/EP2012/065394 filed Aug. 7, 2012. PCT/EP2012/065394 claims priority to European patent application 11176770.3 filed Aug. 8, 2011. The disclosures of both European patent application 11176770.3 and PCT/EP2012/065394 are hereby incorporated herein by reference.

TECHNICAL FIELD

The present invention relates to a separation material comprising a matrix that is bound to a saccharide, enabling the separation from a liquid of substances that selectively bind the saccharide. The present invention further relates to a method for preparing a separation material for separating substances from a liquid that selectively bind a saccharide of the separation material and a method for separating substances from a liquid that selectively bind a saccharide of the separation material. The present invention also relates to a device comprising a separation material for separating substances from a liquid that selectively bind to the saccharide of the separation material.

BACKGROUND OF THE INVENTION

EP 1 165 159 B1 describes a column for treatment of whole blood or blood plasma, to a method for extracorporeal removal of blood group A and blood group B antibodies from whole blood or blood plasma, to a saccharide-linker-O-matrix product and to use thereof in the column during the method for extracorporeal removal. The saccharide is a blood group determinant A or a blood determinant B, while the matrix can be a polymer, a plastic or a polysaccharide, especially agarose. The linker is an alkyl that can bear an aromatic moiety, a peptide, a protein or a polysaccharide.

U.S. Pat. No. 7,700,746 B2 discloses a separation material comprising a saccharide coupled to a linker, agarose as matrix coupled to the linker, wherein the linker is an alkyldiamine or an anilyl alkyl alcohol derivative.

While these separation materials show very good properties in separating e.g. blood antibodies, there is still a desire to provide new materials enabling an enhancement of the performance.

SUMMARY OF THE INVENTION

It is an object of the present invention to provide a new separation material for selectively separating substances from a liquid. In one embodiment of the invention, the material is designed to remove anti-A and/or anti-B antibodies from whole blood or plasma.

According to one aspect of the present invention, a separation material of formula (VI) is provided

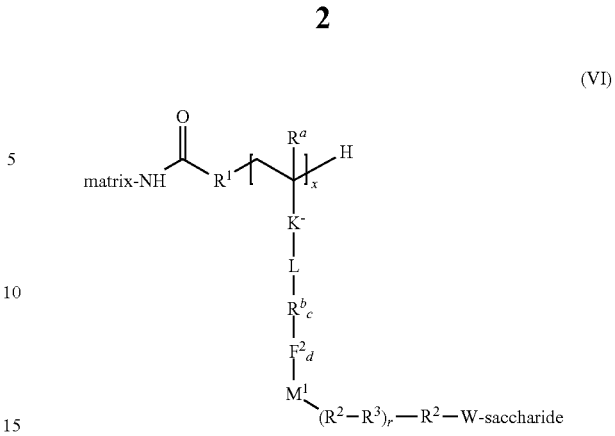

(VI)

wherein
$R^1$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino;
$R^a$ represents —H, methyl or ethyl;
K represents —CO—, —NH— or —CH$_2$—;
L represents —H, —NH— or —O—;
$R^b$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino;
$F^2$ represents —NH—, —CH$_2$—, —C(O)—, —N=, —O—, —CH=, —CH(OH)— or CH$_2$—CH(OH)—;
c and d independently of each other represent 0 or 1;
$M^1$ represents —NH—, —CH$_2$—, —C(O)—, —N=, —O— or —CH=;
$R^2$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, hydroxy, thiol, acylamino, alkoxycarbonylamino, haloalkoxycarbonylamino or alkylsulfonylamino;
$R^3$ represents, independently of each other, —CO—NH—, —NH—CO—, —CO—NH—NH—, —NH—NH—CO—, —CH=N—NH—, —NH—N=CH—, —N=CH—, —CH=N— or triazolyl,
r represents 0 or an integer from 1-10;
W represents —O—, —S—, or NR'—, wherein R' represents H, or methyl; and
x represents an integer from 1-50, from 1-30, from 1-20 or from 1 to 10.

According to one aspect of the invention, the separation material of formula (VI) can be produced by a) providing a matrix of formula (I),
b) providing a thermally labile radical initiator of formula (II),
c) providing at least one polymerizable monomer of formula (III),
d) providing at least one saccharide of formula (V),
e) coupling the matrix to the thermally labile radical initiator,
f) contacting the matrix surface with a solution of the at least one polymerizable monomer under conditions, where thermally initiated graft copolymerization of the monomers takes place, to form a structure of adjacent functional polymer chains on the surface of the matrix bearing functional groups, and
g) coupling the saccharide to the functional polymer chains on the surface of the matrix.

In one embodiment of the invention, the matrix is a synthetic polymer, a peptide or a polysaccharide.

In another embodiment of the invention, the saccharide is a blood group A determinant or/and a blood group B determinant.

According to a further aspect of the invention, a method for producing a separation material comprising the steps of
a) providing a matrix of formula (I),
b) providing a thermally labile radical initiator of formula (II),
c) providing at least one polymerizable monomer of formula (III),
d) providing at least one saccharide of formula (V),
e) coupling the matrix to the thermally labile radical initiator,
f) contacting the matrix surface with a solution of the at least one polymerizable monomer under conditions, where thermally initiated graft copolymerization of the monomers takes place, to form a structure of adjacent functional polymer chains on the surface of the matrix bearing functional groups, and
g) coupling the at least one saccharide to the functional polymer chains on the surface of the matrix,
is provided.

According to another aspect of the invention, a method for selectively separating substances from a liquid using a separation material according to the present invention is provided.

In one embodiment of the invention the liquid is whole blood, blood plasma or a blood product.

According to yet another aspect of the invention, a device for selectively separating substances from a liquid using a separation material according to the present application is provided.

The expression "at least one" as used herein refers to polymerizable monomers or to saccharides of one defined formula, respectively, and is not meant to designate a single molecule of the respective compound.

SHORT DESCRIPTION OF THE FIGURES

FIG. 1

Figure 1B:
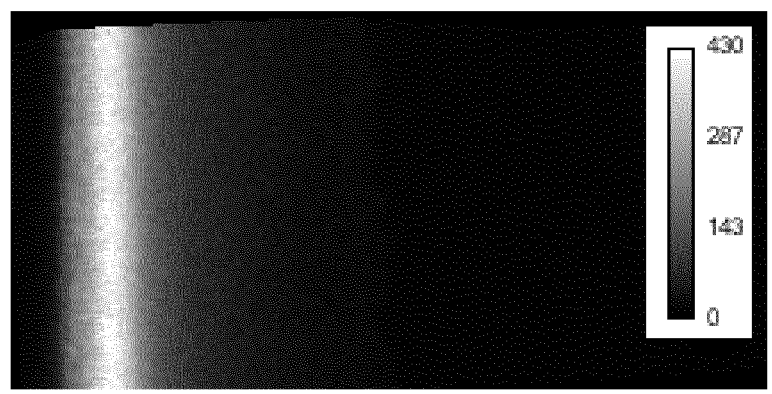

FIG. 1B shows a two photons excitation microscopy image of a plasma amino functionalized hollow fiber membrane having a wall thickness of 50 μm. Also shown is the relative fluorescence spectrum (FIG. 1A). The amino functions were reacted with 4-fluoro-7-nitrobenzo-2-oxa-1,3-diazole (NBD-F) as fluorophore. The area of the image is 100 μm×50 μm. The x-axis of the spectrum shows the width in μm, the y-axis the relative fluorescence intensity.

FIG. 2

Figure 2:
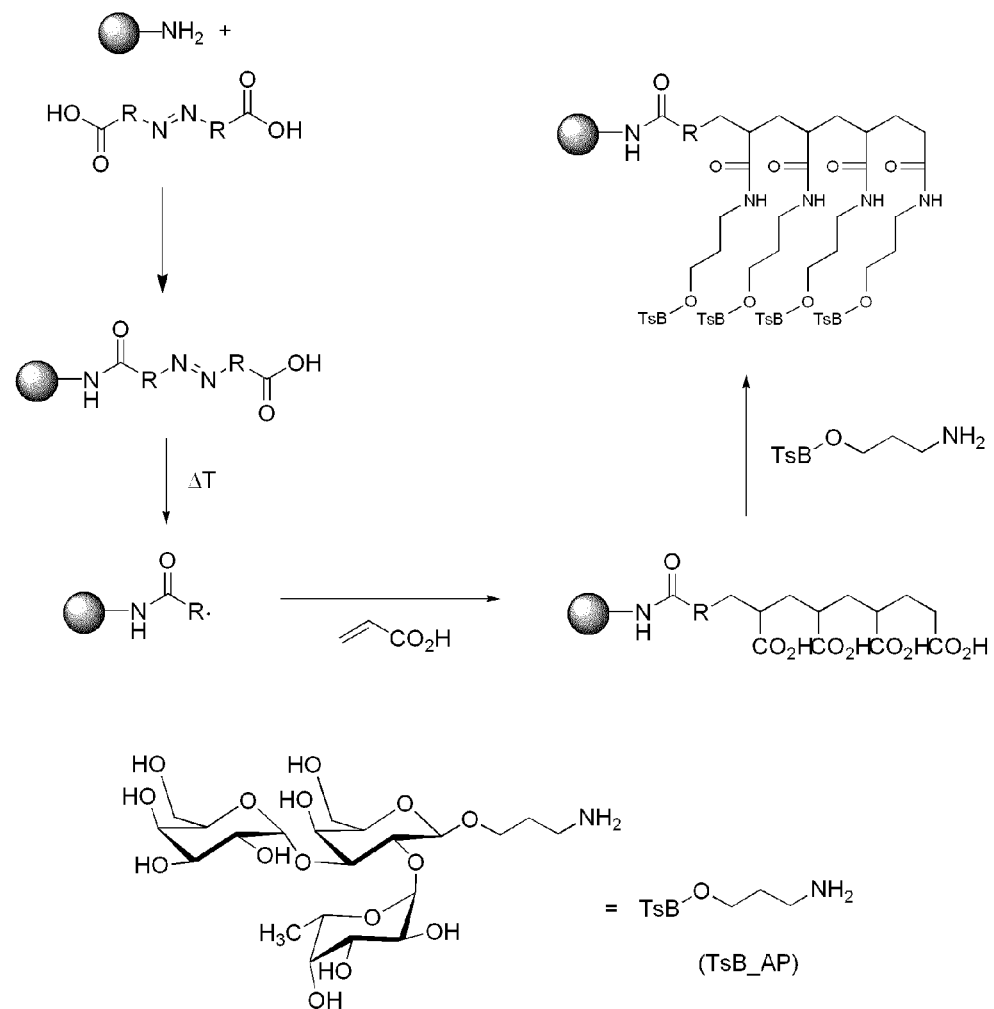

FIG. 2 shows an example of a typical synthesis design for preparing a separation material according to the invention. An amino-functionalized matrix is reacted with a radical initiator, followed by graft co-polymerization with acrylic acid and coupling of a blood group B trisaccharide (Ts-B_AP).

DETAILED DESCRIPTION

In one embodiment of the invention, a separation material of formula (IV) is provided

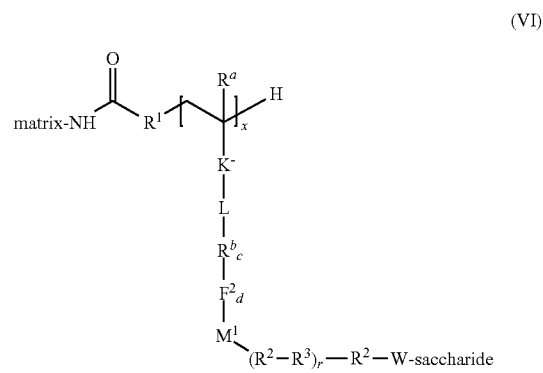

(VI)

wherein
$R^1$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino;
$R^a$ represents —H, methyl or ethyl;
K represents —CO—, —NH— or —CH$_2$—;
L represents —CH$_2$—, —NH— or —O—;
$R^b$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino;
$F^2$ represents —NH—, —CH$_2$—, —C(O)—, —N=, —O—, —CH=, —CH(OH)— or CH$_2$—CH(OH)—;
c and d independently of each other represent 0 or 1;
$M^1$ represents —NH—, —CH$_2$—, —C(O)—, —N=, —O— or —CH=;
$R^2$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, hydroxy, thiol, acylamino, alkoxycarbonylamino, haloalkoxycarbonylamino or alkylsulfonylamino;

$R^3$ represents, independently of each other, —CO—NH—, —NH—CO—, —CO—NH—NH—, —NH—NH—CO—, —CH=N—NH—, —NH—N=CH—, —N=CH—, —CH=N— or triazolyl, r represents 0 or an integer from 1-10;

W represents —O—, —S—, —CH$_2$— or —NR'—, wherein R' represents H, or methyl; and x represents an integer from 1-50, from 1-30, from 1-20 or from 1 to 10.

In one embodiment of the invention, $R^b$ represents, independently of one another, straight-chain or branched methyl, ethyl, n- or iso-propyl, n-, iso-, sec- or tert-butyl, n-pentyl, n-hexyl, n-heptyl, n-octyl, n-nonyl or n-decyl groups, wherein the alkyl group can be unsubstituted, or substituted with at least one suitable substituent selected from the group of substituents comprising halogen, alkyl, alkoxy, haloalkyl, cyano, nitro, amino, amidino, hydroxy, thiol.

In another embodiment of the invention, K represents —C(O)—. In yet another embodiment of the invention, L represents —NH— or —O—. In yet another embodiment of the invention c is 1 and $R^b$ is methyl, ethyl, n- or iso-propyl, n-, iso-, sec- or tert-butyl, n-pentyl or n-hexyl. In yet another embodiment of the invention, c is 0 and d is 1. In yet another embodiment, $F^2$ is —NH—, —CH$_2$—, —C(O)—, —O—, —CH(OH)— or CH$_2$—CH(OH)—. In yet another embodiment, c and d are 0. In yet another embodiment, r is 0. In yet another embodiment, $M^1$ is —NH— or —C(O)—. In yet another embodiment, $R^2$ is straight-chain, unsubstituted $C_1$-$C_{10}$ alkyl. In yet another embodiment, W is —O—.

In another embodiment of the invention, K represents —C(O)—, L represents —NH— or —O, c is 1 and $R^b$ is methyl, ethyl, n- or iso-propyl, n-, iso-, sec- or tert-butyl, n-pentyl or n-hexyl. In yet another embodiment of the invention, c is 0 and d is 1 and $F^2$ is —NH—, —CH$_2$—, —C(O)—, —O—, —CH(OH)— or CH$_2$—CH(OH)—. In yet another embodiment, c and d are 0. In yet another embodiment, r is 0, $M^1$ is —NH—, $R^2$ is straight-chain, unsubstituted $C_1$-$C_{10}$ alkyl, and W is —O—.

In one embodiment of the invention, a matrix of the general formula (I)

$$N^1\text{-matrix} \quad (I),$$

wherein $N^1$ represents H$_2$N—, H$_2$N—NH—, or epoxy, is reacted with a thermally labile radical initiator of the general formula (II)

$$HO_2C—R^1—Y—R^1—CO_2H \quad (II),$$

wherein

Y represents —N=N—, or —O—O—, and $R^1$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino.

In one embodiment of the invention, $N^1$ is H$_2$N— or epoxy.

In another embodiment of the invention, the epoxy functions of the matrix are transformed into amino functions by reaction with ammonia solution prior to the coupling with the radical initiator of formula (II).

In one embodiment of the invention, Y represents —N=N—.

Useful thermally labile radical initiators include compounds which decompose to give free radicals on thermal activation. In one embodiment of the invention, the thermally labile radical initiator is selected from the group comprising azo compounds or peroxides.

In one embodiment of the invention, the thermally labile radical initiator is 4,4'-azobis-(4-cyanovaleric acid) or 2,2'-azobis-[N-(2-carboxyethyl)-2-methylpropionamidine.

In one embodiment of the invention, the thermally labile radical initiator is 4,4'-azobis-(4-cyanovaleric acid).

The coupling reaction between the carboxylic group of the thermally labile radical initiator and the amine-functions on the matrix can be carried out according to any procedure known to the person skilled in the art. A common method comprises the activation of the carboxylic acid with a carbodiimide, thus facilitating the coupling to an amine. The formation of an amide using a carbodiimide is straightforward, but with several side reactions complicating the subject. The carboxylic acid reacts with the carbodiimide to produce the key intermediate, an O-acylurea, which can be referred to as a carboxylic ester with an activated leaving group. The O-acylurea then reacts with amines to give the desired amide and urea as byproduct. Additives are often added to increase yields and decrease side reactions. These substances can react with the O-acylurea to form an active ester which is less reactive and less in danger of racemization.

Examples of suitable carbodiimides include dicyclohexylcarbodiimide (DCC), diisopropylcarbodiimide (DIC) and 1-ethyl-3-(3-dimethylaminopropyl)carbodiimide (EDC).

Examples of suitable additives include N-hydroxybenzotriazole (HOBt), 1-Hydroxy-7-azabenzotriazole (HOAt), N-hydroxysuccinimide (NHS), and N-hydroxysulfosuccinimide (Sulfo-NHS). An alternative to HOBt and HOAt is ethyl 2-cyano-2-(hydroxyimino)acetate (trade name Oxyma Pure), which is not explosive and has a reactivity of that in between HOBt and HOAt.

Recent reaction schemes totally omit any carbodiimides, introducing the active ester as an uronium or phosphonium salt of a non-nucleophilic anion (tetrafluoroborate or hexafluorophosphate), such as, for example, 2-(1H-benzotriazole-1-yl)-1,1,3,3-tetramethyluronium hexafluorophosphate (HBTU), 2-(7-aza-1H-benzotriazole-1-yl)-1,1,3,3-tetramethyluronium hexafluorophosphate (HATU), 2-(6-Chloro-1H-benzotriazole-1-yl)-1,1,3,3-tetramethylaminium hexafluorophosphate (HCTU), 2-(1H-benzotriazole-1-yl)-1,1,3,3-tetramethyluronium tetrafluoroborate (TBTU), O-(7-azabenzotriazole-1-yl)-N,N,N',N'-tetramethyluronium tetrafluoroborate (TATU), O—(N-Succinimidyl)-1,1,3,3-tetramethyl uranium tetrafluoroborate (TSTU), benzotriazol-1-yl-oxytripyrrolidinophosphonium hexafluorophosphate (PyBOP). Two uronium types of the coupling additive of Oxyma Pure are also available as COMU and TOTU reagent.

The monomers suitable to form the functional polymer chains on the matrix surface by graft polymerization are described by the formula (III):

$$H_2C=C(R^a)—K-L-R^b_c—F^1_d \quad (III)$$

wherein $R^a$ represents —H, methyl or ethyl,

K represents —CO—, —NH— or —CH$_2$—.

L represents —H, —NH— or —O—, and $R^b$ represents straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino.

In one embodiment of the invention, $R^b$ represents straight-chain or branched unsubstituted alkyl of the formula —$(CH_2)_{1-10}$—.

In another embodiment of the invention, the group of substituents of $R^b$ comprises amino, hydroxy, thiol, or chlorine.

c and d represent, independently of each other, 0 or 1.

$F^1$ represents —OH, —$NH_2$, —H, —$N_3$, —$CO_2H$, —CHO, —NH—$NH_2$, —C≡CH or epoxy.

In one embodiment of the invention, the monomers used in one reaction can be the same or different.

The monomers of formula (III) as well as the resulting functional polymer chains which are formed from the monomers of formula (III) carry terminal functional groups $F^1$ which are able to react with a compound of formula (IV), (IVA) or a saccharide of formula (V). Said functional groups may be —OH, —$NH_2$, —$N_3$, —$CO_2H$, —CHO, —NH—$NH_2$, —C≡CH or epoxy.

In one embodiment of the invention, the said functional groups $F^1$ are selected from $H_2N$—, $N_3$—, HOOC—, $NH_2$—NH— or epoxy.

In one embodiment of the invention, the said functional groups $F^1$ are selected from $H_2N$—, HOOC— or epoxy.

In another embodiment of invention, polymerizable monomers of formula (III) are selected from the group comprising acrylic acid (AA), methacrylic acid (MA), 2-butenoic acid, 4-allyl-benzoic acid, glycidyl acrylate, glycidyl methacrylate (GMA), allyl glycidyl ether, vinyl glycidyl ether, vinyl glycidyl urethane, allylamine, N-(3-aminopropyl)methacrylamide and N-vinylformamide (wherein free amine functions are obtained after amide hydrolysis).

In another embodiment of the invention, the monomers of formula (III) are polymerized in a mixture with inert monomers, in order to increase the hydrophilicity of the polymer or/and to improve the biocompatibility of the materials.

Inert monomers are selected from the group comprising 2-hydroxyethyl methacrylate, 2-hydroxypropyl methacrylate, hydroxymethyl methacrylate, hydroxymethyl methacrylamide, N-vinylpyrrolidone, 2-vinyl pyridine, 4-vinyl pyridine and N-vinyl-2-methylimidazole.

In one embodiment of the invention, the separation material is prepared by coupling the functional polymer chains with a saccharide having the general formula (V)

saccharide-W—$R^2$—$(R^3$—$R^2)_r$-M    (V), wherein

W represents O, S, $CH_2$ or NR', wherein R' represents H, methyl or a suitable protecting group, $R^2$ represents, independently of one another, straight-chain or branched $C_1$-$C_{10}$ alkyl such as methyl, ethyl, n- or iso-propyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, hydroxy, thiol, acylamino, alkoxycarbonylamino, haloalkoxycarbonylamino or alkylsulfonylamino, $R^3$ independently of one another represents —CO—NH—, —NH—CO—, —CO—NH—NH—, —NH—NH—CO—, —CH=N—NH—, —NH—N=CH—, —N=CH—, —CH=N— or triazolyl, r represents 0 or an integer from 1-10, and M represents —COOH, —$NH_2$, —C≡CH, —$N_3$, —NH—$NH_2$ or —OH.

In one embodiment of the invention, M represents —COOH or —$NH_2$.

Suitable protecting groups for amines are acetyl (Ac), trifluoroacetyl (TFA), trichloroacetyl, benzoyl (Bz), benzyl (Bn), tert-butyloxycarbonyl (BOC), carbobenzyloxy (Cbz), p-methoxybenzyl carbonyl (Moz), 9-fluorenylmethyloxycarbonyl (FMOC), vinyloxycarbonyl (Voc), allyloxycarbonyl (Alloc), p-methoxybenzyl (PMB), 3,4-dimethoxybenzyl (DMB), p-methoxyphenyl (PMP), triphenylmethyl (Tr), tosyl (Ts) or nosyl (Ns).

In another embodiment, the separation material is prepared by coupling the functional polymer chains and a saccharide of formula (V) with a compound of the general formula (IV)

$R^{4A}$—$R^2$—$(R^4$—$R^2)_n$-$E^1$    (IV)

wherein $R^2$ is as defined before, $R^4$ independently of one another represents —O—, —S—, —CO—NH—, —NH—CO—, —N=CH— or —CH=N—, n represents 0 or an integer from 1-600, $R^{4A}$ represents HOOC—, $H_2N$—, HC≡C—, $N_3$—, $NH_2$—NH— or OH—, $E^1$ represents —COOH, —CHO, —$NH_2$, —SH, —OH, —$N_3$, —NH—$NH_2$ or —C≡CH.

In one embodiment of the invention $R^{4A}$ represents HOOC— or $H_2N$—, $E^1$ represents —COOH or —$NH_2$, and n represents 0.

In one embodiment of the invention $E^1$ represents —COOH, —CHO, or —$NH_2$. In another embodiment of the invention, $E^1$ represents —$NH_2$ or —COOH.

$R^{4A}$ and $E^1$ may be the same or different.

In one embodiment of the invention, n is 0 and formula (IV) becomes general formula (IVA)

$R^{4A}$—$R^2$-$E^1$    (IVA), wherein $R^{4A}$, $R^2$ and $E^1$ are as defined before.

In another embodiment of the invention, the compound of formula (IVA) may be coupled with at least one further compound of formula (IVA), which may be same or different, before reacting it with the functional polymer chains and/or the saccharide of formula (V). The resulting compound may also be represented by the general formula (IV), wherein $R^{4A}$, $R^2$, $R^4$, n and $E^1$ are as described before. In a specific embodiment of the invention, n is an integer from 2 to 10.

In one embodiment of the invention, the compound of formula (IV) is reacted with the functional polymer chains resulting from the graft polymerization. As described above, the polymerizable monomers and, hence, also the polymer chains, bear suitable functional groups as defined before for the coupling with a compound of formula (IV) or a saccharide of formula (V).

Suitable functional groups for the coupling to a compound of formula (IV) or a saccharide of formula (V) are $H_2N-$, $N_3-$, $HOOC-$, $OHC-$, $NH_2-NH-$, $C\equiv CH-$ or epoxy.

In another embodiment of the invention, the compound of formula (IV) is reacted first with the saccharide of formula (V) and, in a second step, is coupled to the functional polymer chains.

In one embodiment of the invention, the compounds of formula (IV) are selected from the group of compounds comprising dicarboxylic acids of the general formula $HOOC-R-COOH$, diamines of the general formula $H_2N-R-NH_2$ and amino acids of the general formula $H_2N-CHR-COOH$ or $H_2N-(CH_2)_n-COOH$, wherein n is an integer from 1 to 10.

In another embodiment of the invention, the compound of formula (IV) is selected from the group of compounds comprising 2-aminoethanol, 3-aminopropanol, 4-aminobutanol, 5-aminopentanol, 6-aminohexanol, 7-aminoheptanol, 8-aminooctanol, 9-aminononanol, 10-aminodecanol, 1,2-ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 2-aminoethanethiol, 3-aminopropanethiol, 4-aminobutanethiol, 5-aminopentanethiol, 6-aminohexanethiol, 7-aminoheptanethiol, 8-aminooctanethiol, 9-aminononanethiol, 10-aminodecanethiol, 2-hydroxyethanoic acid, 3-hydroxypropanoic acid, 4-hydroxybutanoic acid, 5-hydroxypentanoic acid, 6-hydroxyhexanoic acid, 7-hydroxyheptanoic acid, 8-hydroxynonanoic acid, 9-hydroxydecanoic acid, 2-aminoethanoic acid, 3-aminopropanoic acid, 4-aminobutanoic acid, 5-aminopentanoic acid, 6-aminohexanoic acid, 7-aminoheptanoic acid, 8-aminononanoic acid, 9-aminodecanoic acid, 2-thioethanoic acid, 3-thiopropanoic acid, 4-thiobutanoic acid, 5-thiopentanoic acid, 6-thiohexanoic acid, 7-thioheptanoic acid, 8-thiononanoic acid, 9-thiodecanoic acid, as well as their branched isomers and their unsaturated derivatives.

In yet another embodiment of the invention, the compound of formula (IV) is selected from the group of compounds comprising 2-aminoethanoic acid, 3-aminopropanoic acid, 4-aminobutanoic acid, 5-aminopentanoic acid, 6-aminohexanoic acid, 7-aminoheptanoic acid, 8-aminononanoic acid and 9-aminodecanoic acid. In yet another embodiment of the invention, the compound of formula (IV) is 6-aminohexanoic acid.

In yet another embodiment of the invention, the compound of formula (IV) is selected from the group of compounds comprising 1,2-ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine and 1,10-decylenediamine.

In yet another embodiment of the invention, the compound of formula (IV) is selected from the group of compounds comprising propanedioic acid (malonic acid), butanedioic acid (succinic acid), pentanedioic acid (glutaric acid), hexanedioic acid (adipic acid), heptanedioic acid (pimelic acid), octanedioic acid (suberic acid), nonanedioic acid (azelaic acid), decanedioic acid (sebacic acid), glutathione or dicarboxy-PEG (DC-PEG). In one specific embodiment of the invention, the compound of formula (IV) is selected from glutaric acid or adipic acid. In another specific embodiment of the invention, the compound of formula (IV) is glutathione.

In one embodiment of the invention, the amino function of the functional polymer chains may react with a compound of formula (IV) wherein $E^1$ is carbonyl and form an imine or a Schiff base as linkage.

In another embodiment of the invention, the amino function of the functional polymer chains is transformed to carry an azide function, the azide being suitable for a click chemistry reaction with a terminal alkyne $E^1$ of the compound of formula (IV), leading to a triazolyl group as linkage.

In a further embodiment of invention, the functional group of the polymer chains is a carboxyl group which is reacted with an amine function $E^1$ of the compound of formula (IV), leading to an amide group as linkage.

In yet a further embodiment, the functional polymer chains carry alkyne moieties on their surface. The alkyne groups of the functional polymer chains are transformed into triazolyl groups via cycloaddition with an azide group $E^1$ of the compound of formula (IV).

In yet a further embodiment, the functional polymer chains carry hydrazine functions. A hydrazide linkage is then formed by reaction of the hydrazine with the carboxyl function $E^1$ of a compound of formula (IV). Alternatively, the hydrazine group can be present as $E^1$ on a compound of formula (IV), whereas the functional polymer chains carry accessible carboxyl groups on their surface.

In a yet further embodiment, the functional polymer chains carry an epoxy function. A secondary amine function is formed by the reaction of the epoxy function of the functional polymer chains and a primary amino function $E^1$ of a compound of formula (IV).

Alternatively, the epoxy function of the functional polymer chains may be reacted with a thiol function of $E^1$, leading to a thioether.

TABLE I

Reaction schemes for various combinations of functional polymer chains grafted on a matrix of formula (I) and a compound of formula (IV).

| | Matrix with functional group | Compound coupled to the matrix | Product |
|---|---|---|---|
| 1 | ●-$NH_2$ | $HO_2C$-♦ | ●-NH—CO-♦ |
| 2 | ●-$NH_2$ | OHC-♦ | ●-N=CH-♦ |
| 3 | ●-$N_3$ | HC≡C-♦ | ●-triazole-♦ |
| 4 | ●-$CO_2H$ | $H_2N$-♦ | ●-CO—NH-♦ |
| 5 | ●-NH—$NH_2$ | $HO_2C$-♦ | ●-NH—NH—CO-♦ |
| 6 | ●-NH—$NH_2$ | OHC-♦ | ●-NH—N=CH-♦ |
| 7 | ●-epoxy | $H_2N$-♦ | ●-C(OH)—$CH_2$—NH-♦ |

The symbol "●" represents the matrix. The compounds which are coupled to the matrix are the compounds of formula (IV), (IVA), a saccharide-bound version thereof or a saccharide of formula (V). Accordingly, only $E^1$/M is shown, whereas the remaining molecule is represented by the symbol "♦". The reactions shown here depict the various possibilities for forming a linkage between a compound of formula (IV), (IVA), a saccharide-bound version thereof or a saccharide (V).

In one embodiment of the invention, a compound of formula (IV) may be used to directly synthesize the separation material by coupling it, successively, first to the functional polymer chains and then to the saccharide (V), or vice versa (Table II).

Compounds of the formula (IV) may be formed by reacting at least two compounds of formula (IVA), wherein $R^{4.4}$ and $E^1$ are different and are chosen in a way which allows a reaction between $R^{4.4}$ of one compound of formula (IVA) with $E^1$ of another compound of formula (IVA). The compounds of formula (IVA) may be the same or different.

In one embodiment of the invention, a compound of formula (IV) is formed and subsequently coupled to the functional polymer chains and the saccharide of formula (V) via a remaining group $R^{4.4}$ and a remaining group $E^1$, respectively.

In one embodiment of the invention (Table II), a compound of formula (IV) is, in a first step, coupled via $R^{4.4}$ to a saccharide of formula (V) and a second compound of formula (IV) is coupled to the functional polymer chains via $E^1$ as described before. In a second step, the linker is being formed by coupling the respective products via the remaining terminal functions $R^{4.4}$ and $E^1$. In one specific embodiment of the invention, the compound of formula (IV) which is bound to the saccharide may be the same as the compound of formula (IV) which is bound to the functional polymer chains. In another specific embodiment of the invention, the compound of formula (IV) which is bound to the saccharide may be different from the compound of formula (IV) which is bound to the functional polymer chains.

In yet another embodiment of the invention, a first compound of formula (IV) is coupled to the saccharide, followed by reacting the attached compound having a free $E^1$ group to at least one additional compound of formula (IV). The resulting molecule is then reacted with the functional polymer chains (Table II). For example, a first compound of formula (IV) may be coupled to the saccharide, wherein the resulting compound has, at its free end, an amine function. This amine function can then be reacted with a dicarboxylic acid, followed by attaching the free carboxylic function of the coupled dicarboxylic acid to an amine group of the functional polymer chains.

TABLE II

Schematic representations of coupling strategies for arriving at the separation material of the present application.

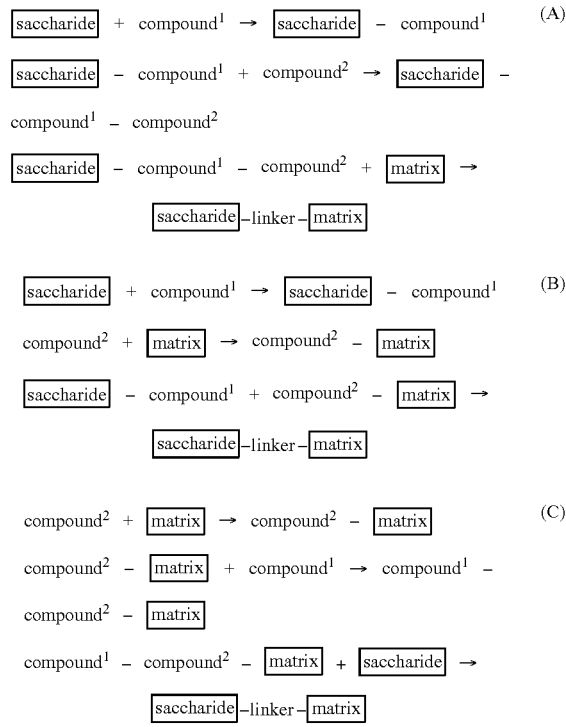

TABLE II-continued

Schematic representations of coupling strategies for arriving at the separation material of the present application.

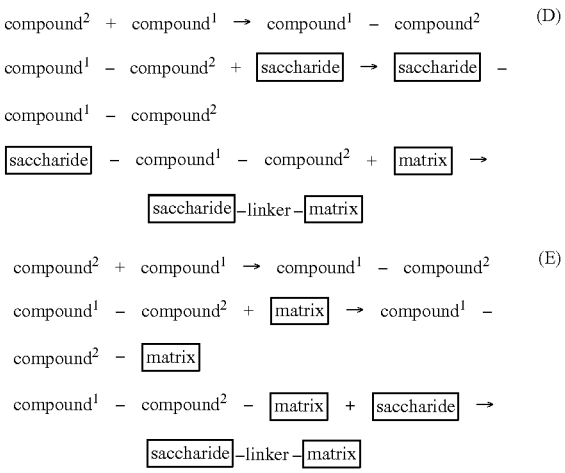

The term "compound[1]" or "compound[2]" refers to compounds of formula (IV). "compound[1]" and "compound[2]" may be the same or different. The term "saccharide" refers to a saccharide compound of formula (V). The term "matrix" in this table refers to the modified matrix after coupling of the radical initiator and graft polymerization, leading to a modified matrix bearing functional polymer chains.

In yet another embodiment of the invention, the compound of formula (IV) which has been coupled to the saccharide has a free carboxy group which is then coupled to a second compound of formula (IV) which is a diamine, resulting in an elongation of the linker. The remaining free amino group may then be reacted, for example, with a dicarboxylic acid, resulting in a terminal carboxy group which may then be coupled to functional polymer chains with amino groups on their surface. Alternatively, the free amino group may directly be coupled to functional polymer chains having carboxy or epoxy groups on their surface.

In another embodiment of the present invention, at least two compounds of formula (IV) are successively coupled to the functional polymer chains, followed by coupling the resulting product to the saccharide (Table II). The at least two compounds of formula (IV) may also be coupled to each other in a first step and then linked to the functional polymer chains, followed by coupling of the saccharide of formula (V).

In a yet another embodiment, the separation material is formed by reacting a compound of formula (IV) to a saccharide of formula (V), followed by reacting the resulting molecule to the functional polymer chains or vice versa (Table II).

In one embodiment of the invention, the coupling reaction is carried out by linking a carboxyl with an amine function. The formation of amide bonds can be carried out as described above.

In one embodiment of the invention, the coupling reaction is carried out by triazole formation. The formation of triazoles from an azide and an alkyne, also known as the alkyne azide Huisgen cycloaddition, is carried out as a 1,3-cycloaddition.

A notable variant of the Huisgen 1,3-dipolar cycloaddition is the copper(I) catalyzed variant, in which organic azides and terminal alkynes are united to afford 1,4-regioisomers of 1,2,3-triazoles as sole products. This reaction is termed the copper(I)-catalyzed Azide-Alkyne Cycloaddition (CuAAC). While the reaction can be performed using commercial sources of copper(I) such as cuprous bromide or iodide, the reaction works much better using a mixture of copper(II) (e.g. copper(II) sulfate) and a reducing agent (e.g. sodium ascorbate) to produce Cu(I) in situ. As Cu(I) is unstable in aqueous solvents, stabilizing ligands are effective for improving the reaction outcome, especially if tris-(benzyltriazolylmethyl)amine (TBTA) is used. The reaction can be run in a variety of solvents and mixtures of water and a variety of (partially) miscible organic solvents including alcohols, DMSO, DMF, tBuOH, dioxane, acetone and mixtures thereof.

Further, the reaction can be catalyzed by ruthenium instead of copper. The ruthenium-catalyzed 1,3-dipolar azide-alkyne cycloaddition (RuAAC) gives 1,5-triazoles. Unlike CuAAC in which only terminal alkynes react, in RuAAC both, terminal and internal alkynes, can participate in the reaction.

The azide functional group can be obtained according to standard procedures. For example, the azide functional group can be obtained by reacting an amine function with an azo-transfer compound, such as, for example, trifluoromethanesulfonyl azide or imidazole-1-sulfonyl azide. Alternatively, the azide can be formed by the reaction of an alkyl or benzyl chloride, bromide or tosylate with sodium azide in aqueous solution and by applying microwaves.

Alkynes can be obtained according to standard procedures. Specialty alkynes are prepared by dehydrohalogenation of vicinal alkyl dihalides or vinyl halides. Metal acetylides can be coupled with primary alkyl halides. Via the Fritsch-Buttenberg-Wiechell rearrangement, alkynes are prepared from vinyl bromides. Alkynes can be prepared from aldehydes using the Corey-Fuchs reaction and from aldehydes or ketones by the Seyferth-Gilbert homologation. In the alkyne zipper reaction, terminal alkynes are generated from internal alkynes by treatment with a strong base.

In one embodiment of the invention, the reaction solvent for each reaction step is a single solvent or a mixture of two or more solvents selected from the group comprising water, alcohols, DMSO, DMF, tBuOH, acetone, 1,4-dioxane or mixtures thereof.

The term "saccharide" as used in the present invention as such or within formula (V) refers to monosaccharides, disaccharides, trisaccharides or oligosaccharides, or polysaccharides. In the context of the present invention, the term may further be defined as a carbohydrate containing molecule or derivative thereof that has biological or any other sort of affinity to another molecule, protein or cell. In one embodiment of the invention, the term "saccharide" refers to a disaccharide, trisaccharide, tetrasaccharide or pentasaccharide.

Saccharides according to the invention may also comprise saccharides which are otherwise linked to proteins in glycoproteins, to lipids in glycolipids. Further, the saccharides according to the invention may have been produced by enzymatic synthesis, by chemical synthesis, recombinant techniques, isolation from natural sources or by a combination of these methods.

In one embodiment of the invention, the saccharide may be a monosaccharide such as, for example, arabinose, lyxose, ribose, ribulose, xylose, xylulose, allose, altrose, glucose, Mannose, gulose, idose, galactose, talose, psicose, fructose, sorbose, tagatose, their respective uronic acids, N-acetylgalactosamine, N-acetylglucosamine, fucose, fuculose, deoxyribose, rhamnose or combinations or modified versions thereof. Modifications may be present on one or more of the saccharides' hydroxyl groups or n-acetyl groups. Further, the di-, tri-, tetra- and pentasaccharides as well as higher oligosaccharides may be formed by a combination of the above listed monosaccharides, wherein the saccharide—which is glycosidically coupled to the linker— has a α—or β-configuration to the linker moiety.

In another embodiment of the invention, the term "saccharide" as used herein alone or within formula (V) is a disaccharide such as, for example, sucrose, lactulose, lactose, maltose, trehalose, isomaltose, or cellobiose.

In yet another embodiment of the invention, the term "saccharide" as used herein alone or within formula (V) is a trisaccharide. Trisaccharides are oligosaccharides consisting of three monosaccharides which are connected by two glycosidic bonds. Analogous to disaccharides, each glycosidic bond can be formed between any hydroxyl group of the underlying monosaccharides. Different bond combinations (regiochemistry) and stereochemistry (alpha- or beta-) are possible, also between the same monosaccharide moieties, which results in triaccharides that are diastereoisomers with different chemical and physical properties.

In one embodiment of the invention, the saccharide is a Galα1-3Gal type of saccharide. In a specific embodiment of the invention, the saccharide is a blood group determinant. Examples for such saccharides are Galα1-3Gal types of saccharides, comprising, inter alia, blood group determinants A (α-L-Fuc-(1→2)-[α-D-GalNAc-(1→3)]-D-Gal) and B (α-l-Fuc-(1→2)-[α-D-Gal-(1→3)]-D-Gal). These types of saccharides can be employed for binding the respective blood group antibodies, for example before or after transplantation, thus reducing the antibody concentration in the patient's blood or plasma, or for isolating said antibodies from blood.

In a further embodiment of the invention, the term "saccharide" as such or within formula (V) means carbohydrate structures which are specific for toxins, viruses, bacteria and/or cells and may be used for the preparation of separation material for the removal or isolation of any such materials. Such saccharides specific for pathogens, toxins, viruses, bacteria and cells have been described before in literature and can be equally effectively coupled to a matrix according to what is described in the present application. The separation material may then be used to purify, isolate or eliminate proteins, peptides, toxins, viruses, cells and/or bacteria from whole blood, plasma, culture media, food products, water or other materials.

In another embodiment of the invention, a separation material according to the present invention comprises carbohydrate structures which are derived from cell surface glycolipids and glycoproteins, generally referred to as tumor or cancer-antigens, may be produced according to the present invention. Such antigens may be recognized by antibodies, for example in connection with prostate-, breast-, intestine- or skin-cancer. Such material may then be used, for example, for isolating such tumor antigen binding antibodies from whole blood, blood plasma, from cell culture media or any other medium the antibodies need to be isolated from. After elution from the separation material, the antibodies can be used for treating said cancer diseases, for example in immunotherapy treatment of cancer.

All suitable matrix materials can be applied for producing the separation material according to the present invention. The term "matrix" as used herein in general or within formula (I) may represent a synthetic polymer, a peptide or a polysaccharide.

In one embodiment of the invention, the term "matrix" represents a polysaccharide. Suitable polysaccharides are, for example, cellulose, nitrocellulose, chitosan, collagen, starch and cross-linked polysaccharide gels such as agarose, Sephadex or Sepharose. Methods for preparing derivatives of polysaccharide matrices have long been known and are, for example, described in U.S. Pat. Nos. 4,411,832 or 3,947,352.

In another embodiment of the invention, the term "matrix" represents a peptide matrix, wherein the functionality $F^1$ of formula (I) may be an integral part of such peptide matrices. Peptide matrices may be generated by the ability of certain peptides to self assemble into macroscopic membranes useful, for example, for in vitro culturing of cells and biomaterial applications. Examples for such peptide matrices are described, for example in U.S. Pat. Nos. 5,670,483, 5,955,343, 6,548,630 and 6,800,481, which relate to amphiphilic peptides having alternating hydrophobic and hydrophilic residues, and their resultant macroscopic membranes. US 2005/0181973 also discloses a self-assembling peptide which may form into a macroscopic membrane.

Synthetic polymeric matrices comprise hydrophilic and hydrophobic synthetic polymers and combinations thereof. The polymers may be selected from the group comprising polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allylbenzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers or any of these polymers modified by introduction of functional groups.

In one embodiment of the invention, the synthetic matrix comprises polymers selected from polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyurethane (PU), polyethylene glycol (PEG), polyvinylpyrrolidone (PVP), polysulfone (PS), polyethersulfone (PES), polyarylethersulfone (PAES) or ethylene vinyl acetate (EVA) and combinations thereof.

In another embodiment of the invention, the synthetic matrix comprises polymers selected from polyacrylate, poly(methyl methacrylate) (PMMA) or polyglycidyl methacrylate (PGMA).

In yet another embodiment of the invention, the synthetic matrix comprises polymers selected from polyvinylpyrrolidone (PVP), polysulfone (PS), polyethersulfone (PES), polyarylethersulfone (PAES) and combinations thereof.

According to one aspect of the present invention, the synthetic material of the matrix per se carries specific functional groups $F^1$ which are needed for coupling a thermally labile radical initiator of formula (II) thereto. For example, many functionalized beads are commercially available and known to a person with skill in the art.

In another embodiment, the polymer material lacks suitable functional groups for the coupling of a thermally labile radical initiator of formula (II) to the matrix. This is especially true for flat sheet or hollow fiber membranes. In such cases a polymer functionalization step is needed. For example, a synthetic material made of an alkane chain like, e.g., polyethylene, does not comprise suitable functional groups for coupling a molecule thereto. Therefore, suitable functional groups have to be introduced chemically after polymer synthesis. A possibility for modifying a polymer is the known method of plasma functionalization which allows, by selection of suitable gas plasma, to introduce functional groups into polymers. This method comprises, for example, the use of ammonia plasma, wherein amino functions are formed on the surface of the treated polymer. Hence, treatment of e.g. polyethylene with ammonia plasma leads to a polyethylene matrix bearing a certain amount of amino functions. These amino groups may afterwards be reacted with a carboxy group of a thermally labile radical initiator of formula (II).

A method for functionalizing a semipermeable hollow fiber membrane in a continuous manner is described, for example, in US 2007/0296105 A1, incorporated herein by reference. The semipermeable hollow fiber membrane is fed through a vacuum system comprising a first vacuum sealed chamber having a pressure of at most 300 mbar, a vacuum sealed plasma ignition chamber having a pressure of at most 0.05 mbar before the introduction of a precursor gas, and a last vacuum sealed chamber having a pressure of at most 300 mbar, and any further vacuum sealed chamber located between any of said chambers, all chambers being consecutively connected in series. When the semipermeable hollow fiber membrane substrate reaches the vacuum sealed plasma ignition chamber, in which a precursor gas containing functional groups has been introduced and has displaced any residual air present therein, the semipermeable hollow fiber membrane substrate is subjected to a plasma ignition, wherein said functional groups in the precursor gas are regioselectively and homogeneously bound to the filtrate side, i.e. the outer membrane layer, and at least to a portion of the pore surface of the semipermeable hollow fiber membrane substrate.

In said method the functional groups comprised introduced by the precursor gas may be amino, carboxyl, aldehyde, ester, epoxy, hydroxyl or sulphonic acids groups.

The precursor gas may be diaminocyclohexane (DACH), diethylenetriamine (DETA) or ammonia. Eventually, a carrier gas like helium, nitrogen, argon, hydrogen or mixtures thereof, is mixed with the precursor gas before or in connection with the addition thereof into the plasma ignition chamber.

In said method the pressure in the vacuum sealed chambers is 5-300 mbar, preferably 0.03-5 mbar, and the pressure in the vacuum sealed plasma ignition chamber is 0.0001-0.05 mbar before the introduction of the precursor gas. After the introduction of the precursor gas the pressure in the vacuum sealed plasma ignition chamber is 0.005-10 mbar, preferably 1.3 mbar.

In one embodiment of said method the ignition frequency during the plasma ignition is 1 kHz-13.56 MHz or multiples of 13.56 MHz or microwave frequency. The power is 50-140 W and the voltage of the electrodes is 50-500 V.

This method allows a density of 10-20 µmol amino functions per g of a hollow fiber membrane.

In another embodiment of the invention, a polymer, e.g. in the form of beads, bearing epoxide groups is treated with ammonia to obtain amino functions for coupling a thermally labile radical initiator of formula (II) to said polymer matrix.

The matrix of formula (I) may be used in form of beads, flat sheet membranes, hollow fiber membranes, or a combination of different geometries in one device.

Suitable beads are, for example, commercially available resins known to a person with skill in the art. In one embodiment of the invention, Tosoh Toyopearl® AF Amino or Epoxy 650-M can be used. Toyopearl® is a methacrylic polymer incorporating high mechanical and chemical stability. Toyopearl® AF-Epoxy 650-M is an activated support resin for affinity chromatography and has an epoxide functionalization of 800 µmol/g. The product is prepared by a high density epoxy functionalization of Toyopearl® HW-65. This material is especially useful when low molecular weight species are to be coupled to the matrix. The particle size distribution is between 40 and 90 µm. Another suitable matrix is Toyopearl® AF-Amino 650-M which is a reactive support resin for affinity chromatography and has 100 µmol/mL amino functions. The product is prepared by introducing amino groups onto Toyopearl® HW-65. Aminoactivated material is able to immobilize ligands with carboxyl or formyl groups.

Another commercially available matrix material is ChiralVision Immobead™ 350. This bead is a crosslinked copolymer of methacrylate carrying 100 µmol/g oxirane groups that is suitable for the covalent immobilization of a variety of enzymes. The porous beads are especially designed to have a low diffusion limitation that allows for the immobilization of enzymes with high specific activities. The particle size distribution is between 300 and 700 µm.

A further commercially available matrix material is Mitsubishi ReliZyme™ EXE 135. The matrix is a crosslinked copolymer of methacrylate containing 166 µmol/g oxirane groups. The median pore diameter is between 40 and 60 nm, while the particle size range is 100-300 µm and 200-500 µm, depending on the product.

According to one aspect of the invention, the saccharides of formula (V) are immobilized via the linker of formula (IV) on the outer surface of plasma separation membranes, modified by graft polymerization as described above. Membranes suitable for plasma separation are known in the art and have been described, for example, in EP 1 875 956 A1 or EP 1 875 957 A1, all incorporated herein by reference. A plasma separation membrane which may be effectively used for preparing a product according to the present invention is an asymmetric plasma separation membrane which exhibits high permeability for the whole spectrum of plasma proteins and lipoproteins, reflected by a high sieving coefficient of >0.90. In plasma separation it is desired to have the total plasma protein in the separated plasma fraction, whereas the larger corpuscular components of the blood, like blood cells and cell debris, are retained by the membrane. Further, such a plasma separation membrane should exhibit a high surface porosity and total porosity of the membrane to achieve high filtration performance. It should also be characterized by a hydrophilic, spontaneously wettable membrane structure, low fouling properties for long term stable filtration, and low protein adsorption. Such a plasma separation membrane preferably has smooth surfaces in contact with blood, thus avoiding or minimizing haemolysis during blood processing. The membrane should show constant sieving properties and filtration behavior over the whole treatment period. It should further exhibit high biocompatibility, low or no complement activation and low thrombogenicity.

Further, the hollow fiber membrane preferably has an inner diameter in the range of 100 to 500 µm. Lower inner diameters are disadvantageous because they result in too high wall shear rates and increased pressure drop in the fiber. On the other hand, if the inner diameters are too high, this would result in too low shear rates which in crease the risk of haemolysis at low transmembrane pressures. The plasma separation membrane which can advantageously be used for the present invention has a wall thickness in the range of 20 to 150 µm. Lower wall thicknesses are disadvantageous due to reduced mechanical properties of the fiber during production and during its use in the plasma separation module itself. Higher wall thicknesses are disadvantageous because they require increased time intervals to perform the phase inversion process resulting in instable process conditions and an instable membrane. Further, the membrane should have a pore diameter on the selective separation layer in the range of 0.1 to 1 µm. Lower average pore diameters are disadvantageous due to incomplete passage of total plasma proteins through the porous structure.

In another embodiment of the invention, the hollow fiber membrane which may serve as a matrix for coupling saccharides thereto is a membrane for haemodialysis, haemofiltration or haemodiafiltration applications as known in the art. Hollow fiber membranes which may serve as a matrix in the present invention are described in EP 2 113 298 A1, EP 2 281 625 A1 or EP 2 228 126 A1, all incorporated herein by reference. In one embodiment of the invention, the membrane is based on polysulfone or polyethersulfone and a blend thereof with low and/or high molecular weight polyvinylpyrrolidone. In one embodiment thereof, a polyvinylpyrrolidone may be used which consists of a low molecular weight component having a molecular weight of below 100 kDa and a high molecular weight component having a molecular weight of 100 kDa or more.

In one embodiment of the invention, the inner layer or lumen of a plasma or ultrafiltration hollow fiber membrane matrix according to the invention, which generally is the blood contacting layer, is not functionalized with a saccharide according to the invention. The saccharide is coupled via a linker to the outer layer of the hollow fibers, and optionally also to at least a portion of the layer connecting the inner layer with the outer layer, i.e. the pores of the membrane. Accordingly, the functionalization with saccharides is present only on the outer filtrate layer and optionally on at least a portion of the pore surface structures connecting the outer and inner layer of the membrane. Such configuration can be applied, for example, for the removal of blood groups antibodies from whole blood, wherein only blood plasma is able to pass from the inner layer to the outer layer, while blood proteins remain on the lumen side of the membrane. As blood plasma diffuses or convects to the outer layer, the antibodies contained in it are bound by the specific matrix supported antigen.

In blood purification applications, activated sites or ligands present on the membrane may activate certain blood constituents, e.g. thrombocytes. Other blood constituents, e.g. leucocytes, red blood cells and proteins, may to some extent be adhered to such ligands or activated sites on the blood side of the membrane. These undesired reactions are significantly reduced or avoided, as thrombocytes, leucocytes, red blood cells and proteins do not come in contact with the activated sites on the membrane, if functionalized membranes according to the invention are used.

Another aspect of the invention is a diffusion and/or separation and/or filtration device comprising a membrane which is functionalized according to the invention. Examples of such devices are dialyzers, hemofilters, and ultrafilters. Such devices generally consist of a housing comprising a tubular section with end caps. A bundle of hollow fiber membranes is usually arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2, all incorporated herein by reference.

In another embodiment of invention, the separation material comprises functionalized beads. The beads may be packed in a column consisting of a housing comprising a tubular section with end caps.

Another aspect of the invention is the use of the separation material of the invention to selectively remove substances from a liquid by selective reaction of these substances with the saccharide moiety of the separation material.

In one embodiment, the separation material of the present invention is used for extra-corporeal removal of blood group A and/or blood group B antibodies from blood, blood plasma or any other blood product. The separation material may be used in the course of different types of organ transplantations as a part of the treatment of the recipient before, during, and eventually after the transplantation. The removal of blood group A and/or blood group B antibodies is needed to minimize the problem of blood group incompatibility between donor and recipient. Either whole blood or blood plasma of the patient who is awaiting, undergoing or has gone through a transplantation procedure may be passed trough the separation material. The separation material may also be used for blood group compatible transplantations, wherein problems in connection with donor and recipient of the same blood group, but of different blood group subgroups are addressed.

In a further embodiment, the separation material is used for purifying, isolating or eliminating glycoproteins, glycopeptides, viruses and/or bacteria in whole or in part from whole blood, plasma, blood products, cell culture media, food products, water or other materials. The expression "blood products" as used herein refers to any component of the blood which is collected from a donor for use in a blood transfusion. Most blood products consist of specific processed components such as red blood cells, blood plasma, or platelets. Further specific examples comprise, for example, cryoprecipitate, PF24, fresh frozen plasma or cryosupernatant.

In another embodiment of the invention, the separation material is used for isolating antibodies from whole blood or blood plasma, wherein said antibodies bind to tumor- or cancer-antigens, for example in connection with prostate-, breast-, intestine- or skin-cancer. After elution from the separation material, the antibodies may be used for treating said cancer diseases, for example by producing pharmaceutically active reagents. The separation material may also be used for removing an excess of antibodies from whole blood or blood plasma during immunotherapy of cancer.

In one embodiment, the separation material of the invention is used in plasmapheresis type applications. In a further embodiment of the invention, the separation material is used in hemodialysis, hemodiafiltration or hemofiltration type applications. The separation material of the invention can be used for these purposes instead of conventional membranes, but in a similar manner. The person skilled in the art will easily derive the necessary modus operandi.

Another aspect of the invention is the use of the separation material of the invention in bioprocessing applications, plasma fractionation and the preparation of protein solutions. The membrane of the invention can be used for these purposes instead of membranes conventionally used for these purposes. The person skilled in the art will easily derive a suitable modus operandi for the intended application.

It will be understood that the features mentioned above and those described hereinafter can be used not only in the combination specified but also in other combinations or on their own, without departing from the scope of the present invention.

The present invention will now be described in more detail in the examples below. The examples are not intended to limit the scope of the present invention, but are merely an illustration of particular embodiments of the invention.

EXAMPLES

Example 1

Reaction of an Amino-functionalized Matrix with a Radical Initiator, Graft Copolymerization with Acrylic Acid and Coupling of a Blood Group B Trisaccharide The separation material of the present invention is produced by coupling an amino resin according to formula (I) with a thermally labile radical initiator according to formula (II), graft polymerization of acrylic acid according to formula (III) leading to a matrix bearing adjacent functional polymer chains, and reaction of the functional polymer chains with a blood group B trisaccharide derivative ("Ts-B_AP") according to formula (V).

In the first reaction step the thermally labile radical initiator according to formula (II) is covalently coupled to the support. Therefore, the amino-group containing support is reacted with activated esters, e.g. carbodiimide or anhydride activated carboxylic groups of the initiator. Thereby, the polymerization initiator is bound to the activated sites. Suitable polymerization initiators according to formula (II) are compounds which decompose to give free radicals at thermal activation, e.g. azo compounds or peroxides, and which further carry reactive substituents, e.g. carboxylic groups.

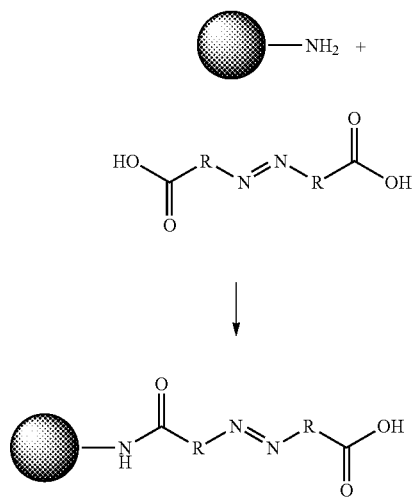
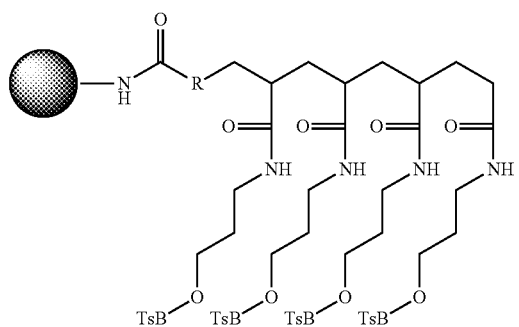
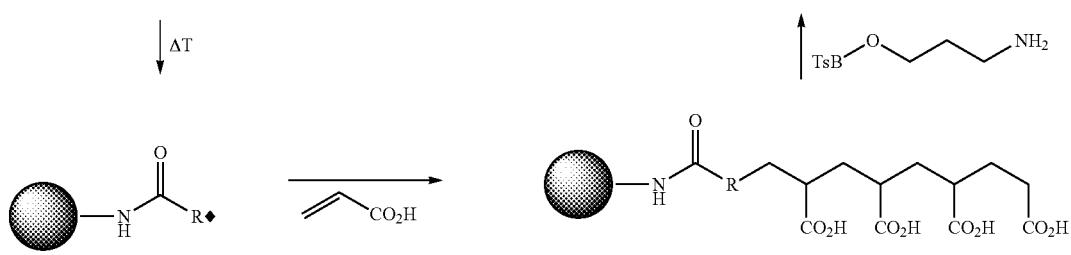
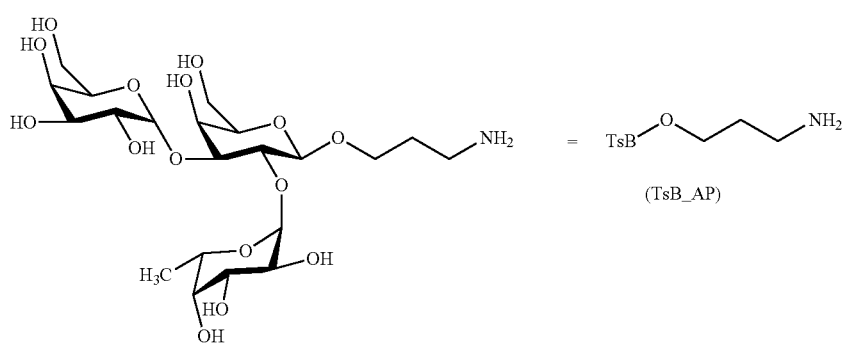

(TsB_AP)

Particularly preferred initiators are azo carboxyl compounds, such as 4,4'-azobis(4-cyanovaleric acid) or 2,2'-azobis[N-(2-carboxyethyl)-2-methylpropionamidine]. The carboxyl groups are activated for example by the water soluble carbodiimide 1-ethyl-3-(3-dimethylaminopropyl)-carbodiimide (EDC) which forms active O-acylurea intermediates. After initial activation by EDC, the carboxyl groups will react with N-hydroxy-succinimide (NHS) to form an active ester, which couples with the primary amino groups on the surface of the substrate. When using 4,4'-azobis(4-cyanovaleric acid) as initiator the reaction can be carried out in organic solutions such as DMF, DMSO, toluene or a mixture thereof. The reaction can also be carried out in aqueous solution at a pH>12, which is preferable for medical applications.

In the second reaction step the initiator immobilized surface is contacted with a solution of acrylic acid. The reaction can be carried out in degassed water in an inert atmosphere. The temperature is chosen above the 10 hour half life temperature of the initiator. The reaction is typically carried out at from 70 to 95° C., and typically takes from 30 min to several hours.

In the last step, a saccharide moiety bearing a free amino function is coupled to the carboxyl functions of the functional polymer chains. A commercially available aminopropyl derivative of blood group B determinant trisaccharide TsB_AP (Dextra Science and Technology Centre, Earley Gate Whiteknights Road, Reading, United Kingdom) is attached to the matrix. The amide formation is accomplished as described for the first step.

Example 2

Reaction of an Amino-functionalized Matrix with a Radical Initiator, Graft Copolymerization with Glycidyl Methacylate and Hydroxylmethyl Methacrylamide, and Coupling of a Blood Group B Trisaccharide In another illustrating example the separating material of the present invention can be produced, for example, using glycidyl methacylate (GMA) as the polymerizable monomer. This type of monomer is used for subsequent binding of affinity ligands such as proteins, peptides, antibodies or other biological molecules. In the present application, the epoxide functions are coupled with saccharides.

Other monomers which comprise both a polymerizable double bond and an oxirane ring are for example glycidyl acylate, vinyl glycidyl ether and vinyl glycidyl urethane. The production of the thus produced separation material is illustrated below.

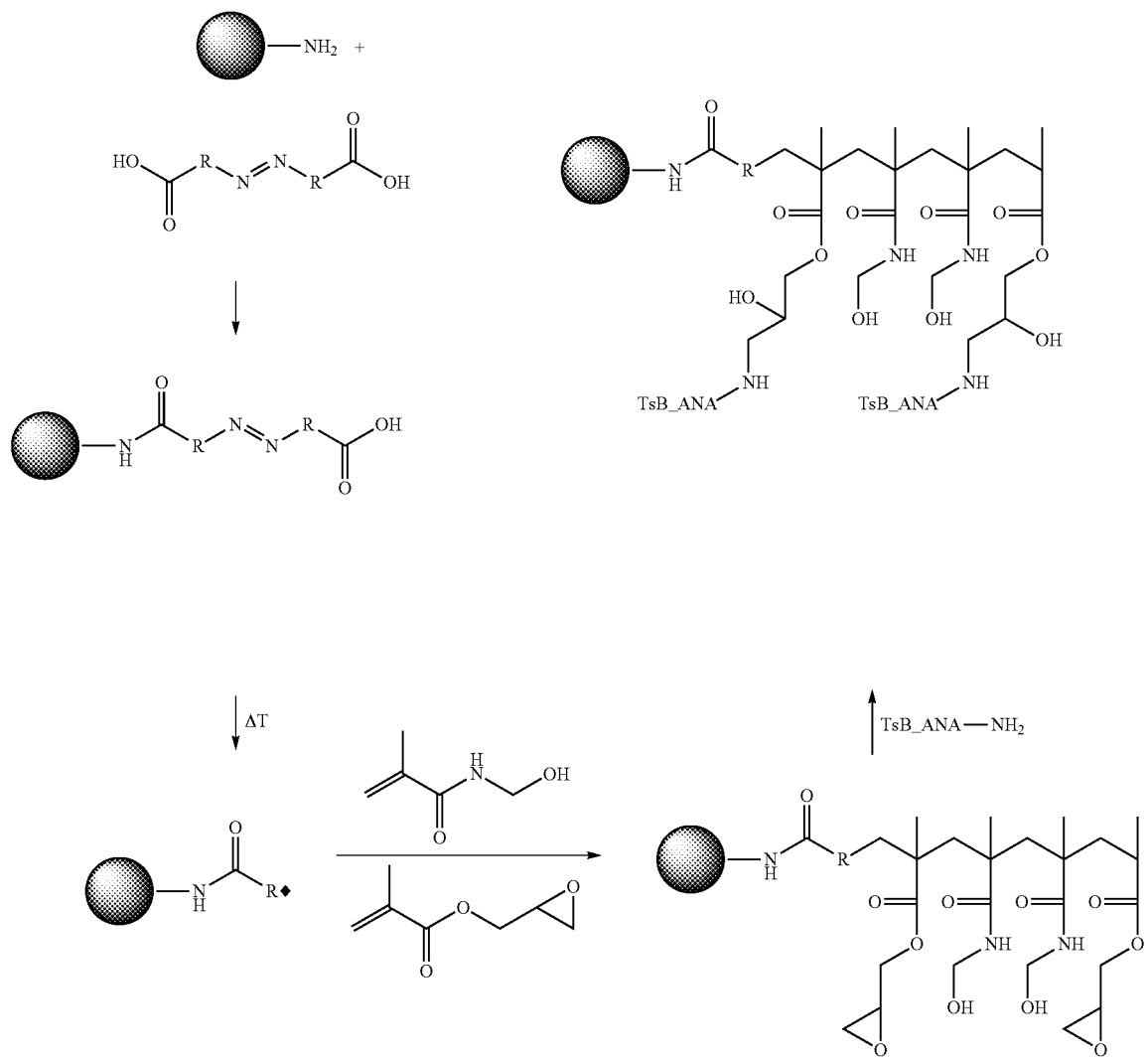

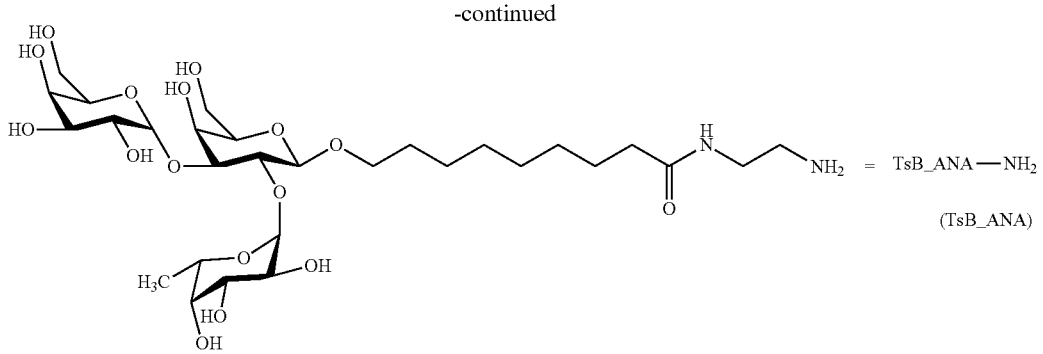

(TsB_ANA)

In this example, glycidyl methacylate (GMA) is polymerized in a mixture with hydroxylmethyl methacrylamide, in order to increase the hydrophilicity of the polymer or/and to improve the biocompatibility of the materials. Suitable inert monomers are 2-hydroxyethyl methacrylate, 2-hydroxypropyl methacrylate, hydroxymethyl methacrylate, N-vinylpyrrolidone, 2-vinyl pyridine, 4-vinyl pyridine and N-vinyl-2-methylimidazole.

In the first reaction step, coupling of polymerisation initiator according to formula (II) is performed as described above in connection with Example 1.

In the second reaction step, the surface is contacted again with a mixture of the monomers according to formula (III) at elevated temperature in an inert atmosphere.

In the last step, a saccharide of formula (V) having a free amino function is coupled to the epoxy functions. The commercially available N-(2-aminoethyl)nonane-1-amide derivative of the blood group B determinant trisaccharide is used here ("TsB_ANA", Carbohydrate Synthesis Ltd, North Culham Estate, Culham Science Centre, Abingdon, Oxford, UK) was applied.

Example 3

Reaction of an Amino-functionalized Matrix with a Radical Initiator, Graft Copolymerization with Glycidyl Methacylate and Hydroxylmethyl Methacrylamide, Azide Formation and Coupling of a Blood Group B Trisaccharide In another example, the coupling of the saccharide according to formula (V) with the functional polymer chains is carried out using a typical click-chemistry reaction, namely the alkyne azide Huisgen cycloaddition under mild conditions. Therefore, the saccharide of formula (V) and the functional polymer chains have to be provided with an azide and an alkyne functionality, respectively.

In the first reaction step, coupling of the radical initiator according to formula (II) is performed as described above in connection with Example 1.

In the second reaction step, the surface is contacted again with a mixture of GMA and hydroxylmethyl methacrylamide at elevated temperature in an inert atmosphere.

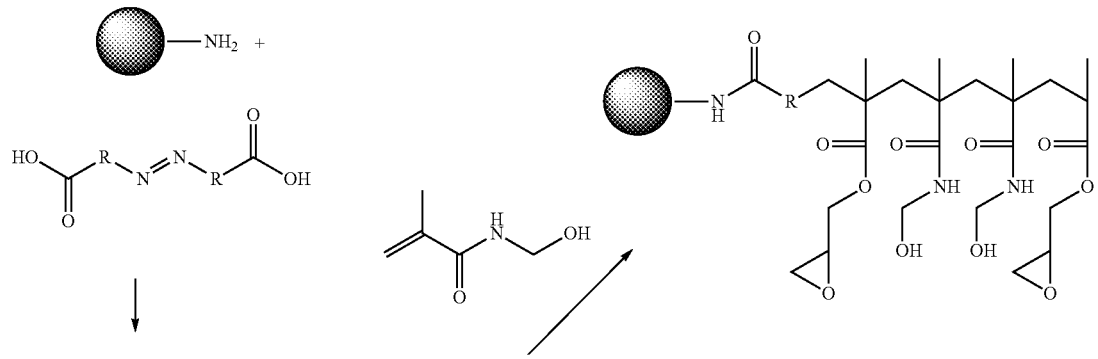

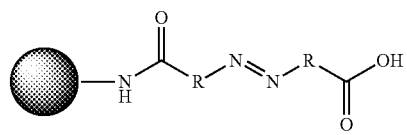

-continued

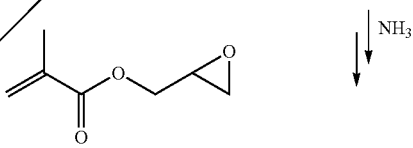

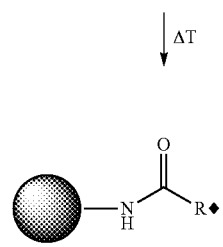

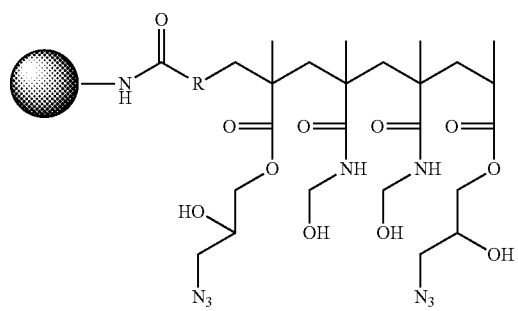

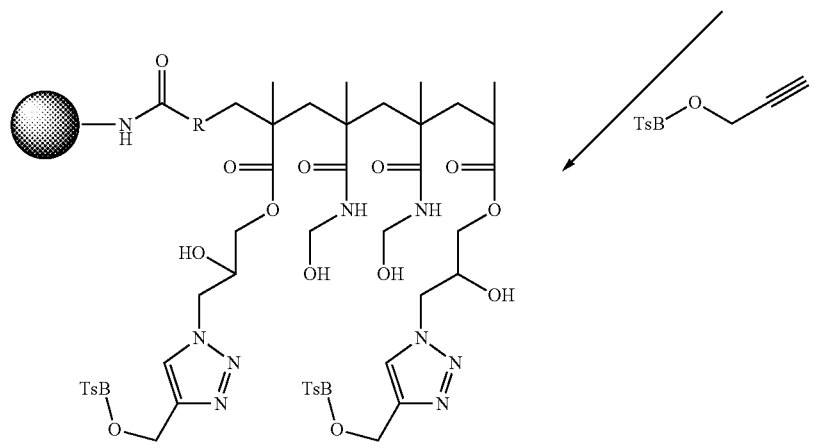

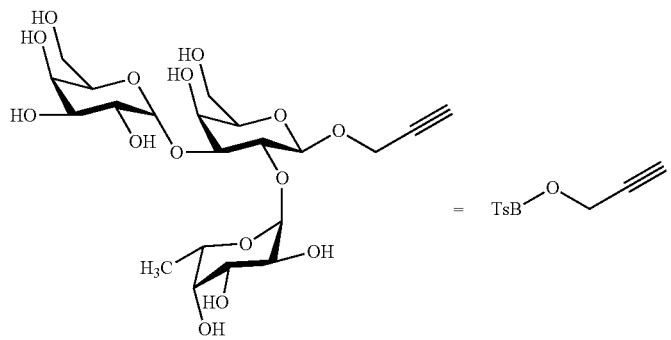

In the next steps, the epoxy functions of the polymerized GMA are treated with ammonia solution to form amino alcohols. The obtained amino functions are transformed into azides, for example by using azo-transfer compounds like trifluoromethanesulfonyl azide and imidazole-1-sulfonyl azide.

In the last step, the azide is reacted, for example under copper catalysis conditions, with a blood group B determinant trisaccharide derivative bearing a terminal alkyne, leading to a linkage via triazole formation.

Example 4

Reaction of an Amino-functionalized Matrix with a Radical Initiator, Graft Copolymerization with Glycidyl Methacylate and Hydroxylmethyl Methacrylamide, Amino Formation, Coupling of Glutaric Acid and Coupling of a Blood Group B Trisaccharide In another example, a matrix (I) is coupled to a thermally labile radical initiator (III), followed by a graft polymerization of a mixture of glycidyl methacylate (GMA) and hydroxylmethyl methacrylamide. The epoxy functions of GMA are then transformed into amino functions (precisely into β-amino alcohols) by reaction with ammonia. The so obtained amino functions are then coupled with a compound of formula (IV), glutaric acid, followed by the coupling of TsB_AP.

Example 5

Resorcinol Test

The quantitative analysis of the amount of saccharide, such as the trisaccharide in Examples 1 to 3, which has been bound to a matrix is carried out by the resorcinol test

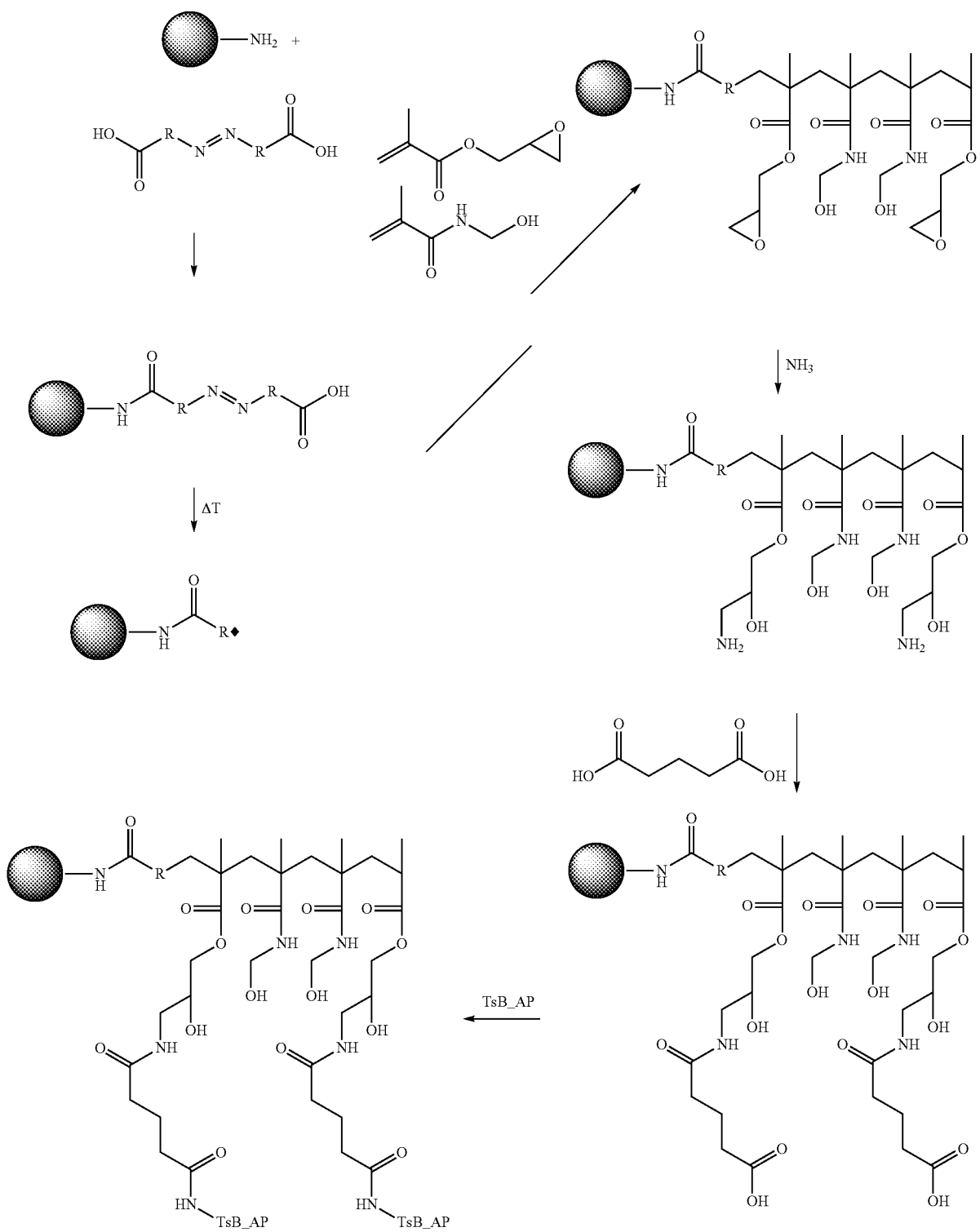

according to Monsigny et al. (*Analytical Biochemistry* 175, 1988, 525-530). 3 mg dry TsB-beads are given into a glass tube together with 200 μL distilled water, 200 μL of an aqueous resorcinol solution (60 mg resorcinol in 10 mL water) and 1 mL of sulphuric acid 75%. The mixture is stirred and heated at 90° C. for 30 min, followed by cooling in a water bath for 30 min in the absence of light, followed by centrifugation. The saccharide content is calculated by measuring the absorption of the solution at 503 nm in a UV/VIS-spectrometer, subtraction of the blank and evaluating the result on a previously created calibration curve.

Example 6

Polyelectrolyte Titration

The analysis of the coupling reactions between the compound of formula (IV) and the functional polymer chains is carried out by quantifying the charges present due to the coupling of a compound of formula (IV). The polyelectrolyte used is cationic polydiallyldimethylammonium chloride (poly-DADMAC) and anionic sodium polyethylensulfonate. The polyelectrolyte titration is carried out with a BTG Mütek PCD-03 Particle Charge Detector.

In case of anionic functional groups on the matrix, 100 mg are stirred overnight with 60 mL 0.001 M poly-DADMAC solution at pH 12. 1 mL of the reaction solution is then titrated in the PCD-03 with 0.001 N sodium polyethylenesulfonate.

Example 7

Transformation of Epoxy Functions on Epoxy-Beads into β-amino Alcohols

Epoxy beads (Toyopearl AF Epoxy 650M, Chiralvision Immobeads T2-150, and Mitsubishi ReliZyme™ EXE 135, respectively) were incubated overnight at room temperature with a 32.0 wt-% ammonia solution in water, in order to transform the epoxy functions into β-amino alcohols. Per gram of beads, 8 mL ammonia solution were applied. In the next step, the beads were rinsed over a glass filter with reverse osmosis water to a neutral pH.

Example 8

Coupling of 4,4'-azobis(4-cyanovaleric Acid) onto Macroporous Acrylic Beads 45 g beads of Example 7 were suspended in 400 ml DMF and 10 g 4,4'-azobis(4-cyanovaleric acid), 15 g EDC and 15 g NHS were added. The batch was agitated for 12 hours at room temperature and afterwards rinsed with water.

Example 9

Graft Polymerisation of Beads with Acrylic Acid 20 g beads of Example 8 were reacted in a reaction solution of 14.4 g acrylic acid in 500 mL water. The reaction was performed with gentle stirring at 75° C. for 18 hours in a $N_2$-atmosphere. The derivatized beads were then thoroughly rinsed with water and dried overnight at 40° C. in a vacuum drying oven. The functionalization of carboxylic functions was determined by polyelectrolyte titration to 1 mmol/g.

Example 10

Graft Polymerisation of Beads with Glycidyl Methacrylate 20 g beads of Example 8 were reacted in a reaction solution of 8.0 g glycidyl methacrylate (GMA) in 120 ml toluene in a three-necked flask. The reaction was performed with gentle stirring at 75° C. for 3 hours in an atmosphere of nitrogen (reflux condenser). The derivatized beads were then thoroughly rinsed and dried overnight at 40° C. in a vacuum drying oven. The degree of grafting was found to be 125%.

Example 11

Coupling of Trisaccharide B of Formula (V) to Carboxy Functions

As blood group determinant B trisaccharide (TsB), two commercially available blood group B trisaccharide derivatives are used. In both derivatives the only free hemiacetal of the trisaccharide (α-l-Fuc-(1→2)-[α-D-Gal-(1→3)]-D-Gal) is reacted with an amino alcohol, leading to an O,O-acetal. The two derivatives differ in the length of the chain attached to the trisaccharide. The first compound is an aminopropyl derivative (TsB_AP), the second is a N-(2-aminoethyl)nonane-1-amide (TsB_ANA).

TsB_AP (1 eq. with respect to the initial functionalization of the beads) and EDC (2 eq. with respect to the initial functionalization of the beads) in 0.25 M phosphate buffer pH 7.4 were gently stirred for 24 h at room temperature with the beads bearing carboxy functions, followed by rinsing with reverse osmosis water. Here, beads grafted with acrylic acid of Example 9 as well as beads grafted with glycidyl methacrylate of Example 10 and reacted with glutathione were applied.

Example 12

Coupling of Trisaccharide B of Formula (V) to Epoxy Functions

TsB_AP (1 eq. with respect to the initial functionalization of the beads) was reacted in 0.1 M borate-KCl buffer pH 10 with glycidyl methacrylate grafted beads of Example 10 at room temperature for 24 h, followed by rinsing with reverse osmosis water.

Example 13

Antibody Titer Reduction Test with TsB-Beads

The following tests were carried out with beads lacking the grafted functional polymer chains.

0.5 mL blood group A plasma was added to 20 mg wet beads of Examples 11 and 12, which roughly correspond to 5 mg dry beads, and was incubated at 37° C. for 120 min over a rotating platform. The probe was then centrifuged (10 min at 1000 g) and the supernatant was used for the determination of IgM antibody titer with a gel test assay which is commercially available from Bio-Rad Laboratories (NaCl, Enzyme Test and Cold Agglutinins ("NaCl cards"); Coombs Anti-IgG ("Coombs cards")). Therefore, serial dilutions of the probe were prepared. 50 µL of plasma or plasma dilution, respectively, were mixed with 50 µL erythrocytes B in NaCl cards and were incubated 15 min at room temperature. In the next step, the probes were centrifuged in an ID-centrifuge (DiaMed AG) and the gel cards were evaluated with regard to agglutination.

Similarly, the IgG antibody titer was determined. First, serial dilutions of the probes were prepared. Then, 50 µL of plasma or plasma dilution, respectively, were mixed with 50 µL erythrocytes B in Coombs cards and were incubated 15 min at room temperature. In the next step, the probes were centrifuged in an ID-centrifuge (DiaMed AG) and the gel cards were evaluated with regard to agglutination.

Tables III and IV summarize the results with beads.

TABLE III

IgM
Tosoh Toyopearls ® AF-Epoxy 650-M

|  | Start titer | End titer |
|---|---|---|
| glutathione + TsB_AP | 1:512 | 1:4 |
| TsB_AP | 1:256 | 1:16 |

TABLE IV

IgG
Tosoh Toyopearls ® AF-Epoxy 650-M

|  | Start titer | End titer |
|---|---|---|
| glutathione + TsB_AP | 1:512 | 1:4 |
| TsB_AP | 1:256 | 1:8 |

Example 14

Plasma Functionalization of a Hollow Fiber Membrane 1000 m of a porous polyaryethersulfone-polyvinylpyrrolidone hollow fiber membrane with an outer shell diameter of 320 µm and a wall thickness of 50 µm were fed through the vacuum sealed plasma ignition chamber with a velocity of 5-20 m/min. Into said ignition chamber a precursor gas consisting of ammonia with a pressure of 0.25 mbar was introduced with a view to depositing an amine containing carbohydrate thin film on the porous surface of the membrane. The plasma was excited with a 13.56 MHz pulsed RF power of 100 W. After this plasma treatment the density of amino groups was measured by polyelectrolyte titration, wherein a value of 20 µmol/g was found.

FIG. 1 shows the result of a two photon excitation microscopy experiment on a hollow fiber membrane having a wall thickness of 50 µm. The amino functions on the membrane formed by plasma functionalization were first reacted with a fluorophore, here 4-fluoro-7-nitrobenzo-2-oxa-1,3-diazole (NBD-F). The excitation occurred by two photons of comparably lower energy than needed for one photon excitation. Each photon carries approximately half the energy necessary to excite the molecule. An excitation results in the subsequent emission of a fluorescence photon, typically at a higher energy than either of the two excitatory photons. The image shows that amino functions are present on the outer surface and within the adjacent 20 µm of the wall. Hence, 40% of the wall is functionalized with amino functions.

Example 15

Preparation of Mini Modules

The preparation of membrane bundles after the spinning process is necessary to prepare the fiber bundle in an adequate way for the experiments. The first process step is to fix 150 fibers near their ends by a filament. The fiber bundle is transferred into a housing. Then, the fiber bundle is cut to a defined length of 20 cm. The next process step consists of transferring the fibers into a potting cap. The potting cap is fixed mechanically, and a potting tube is put over the potting caps. Then, the ends of the fibers are closed. An optical control ensures that all fibers are well closed. Afterwards, the mini module is put into a vacuum drying oven over night before. Then, the potting is done with polyurethane. After the potting, it has to be ensured that the polyurethane can harden for at least one day. In the next process step, the potted membrane bundle is cut to a defined length. The last process step consists of an optic control of the fiber bundle. During this process step, the quality of the cut (is the cut smooth or are there any damages of the knife) and the quality of the potting (is the number of open fibers of the spinning process reduced by fibers that are potted or are there any visible voids where there is no polyurethane) are controlled. After the optical control, the membrane bundles are stored dry before they are used for the different experiments.

Example 16

Preparation of Filters

The filter (=dialyzer) comprises about 8,000 to 10,000 fibers with an effective surface area of 1.4 m$^2$. A filter is characterized by a cylindrical housing with two connectors for the dialyzing fluid and caps applied on both ends, each with one centered blood connector. The manufacturing process (after winding) can be divided into the following main steps:
(A) the cut bundles (length approx. 30 cm) are transferred into the housing with a special bundle claw;
(B) both ends of the bundles are closed by a closing process
(C) the fibers are potted into the housing with polyurethane (PUR);
(D) the ends are cut to open the fibers;

(E) the caps are welded to the blood connectors using ultrasonic welding;
(F) final treatment comprises: rinsing, integrity testing, final drying
(G) the filters are packed in sterile bags and steam sterilized.

Example 17

Coupling of 4,4'-azobis(4-cyanovaleric Acid) onto Microporous Hollow Fiber Membranes A solution of 1.1% of 4,4'-azobis(4-cyanovaleric acid), 1.6% of NHS and 1.6% of EDC in 1250 mL 0.1 M NaOH was reacted with a bundle of hollow fibers of Example 14 in a continuous-flow process in a mini-module at a flow rate of 85 mL/min at 75° C. for 16 h. Afterwards, the excess reagents were removed by washing repeatedly with water. The functionalization of the bundles with carboxy functions was determined by polyelectrolyte titration to 10-20 µmol/g.

Example 18

Grafting on Microporous Hollow Fiber Membranes with Acrylic Acid

The hollow fibers of Example 17 were reacted with a 0.5% aqueous solution of acrylic acid (AA). The reaction was performed in a mini-module at 75° C. for 16 h at a flow rate of 85 mL/min in a nitrogen atmosphere. The derivatized hollow fibers were then rinsed with reverse osmosis water. The functionalization of carboxylic functions was determined by polyelectrolyte titration to 94 µmol/g.

Example 19

Grafting on Microporous Hollow Fiber Membranes with Acrylic Acid

The hollow fibers of Example 17 were reacted with a 1% aqueous solution of acrylic acid (AA). The reaction was performed in a mini-module at 75° C. for 16 h at a flow rate of 85 mL/min in a nitrogen atmosphere. The derivatized hollow fibers were then rinsed with reverse osmosis water. The functionalization of carboxylic functions was determined by polyelectrolyte titration to 166 µmol/g.

Example 20

Grafting on Microporous Hollow Fiber Membranes with Glycidyl Methacrylate

The hollow fibers of Example 17 were reacted with a 2.4% solution of glycidyl methacrylate (GMA) in 1250 mL isopropyl alcohol. The reaction was performed in a mini-module at 75° C. for 16 h at a flow rate of 85 mL/min in a nitrogen atmosphere. The derivatized hollow fibers were then rinsed with reverse osmosis water.

Example 21

Coupling of Trisaccharide B of Formula (V) to Acrylic Acid Grafted Hollow Fiber Membranes One mini-module of hollow fibers of Example 18 was reacted with TsB_ANA (43 µmol) and EDC (86 µmol) in 17 mL 0.1 M MES buffer pH 5.4 at room temperature under continuous flow conditions at a flow rate of 5 mL/min for 24 h. The derivatized hollow fibers were then rinsed with 1.5 L reverse osmosis water.

The same reaction was carried out with TsB_AP.

Example 22

Coupling of Trisaccharide B of Formula (V) to Glycidyl Methacrylate Grafted Hollow Fiber Membranes One mini-module of hollow fibers of Example 20 was reacted with TsB_ANA (43 µmol) in 17 mL 0.1 M borate-KCl buffer pH 10 at room temperature under continuous flow conditions at a flow rate of 6 mL/min for 24 h. The derivatized hollow fibers were then rinsed with 1.5 L reverse osmosis water.

Example 23

Antibody Titer Reduction Test with TsB-hollow Fibers

A mini module comprising 150 hollow fibers of Examples 21 and 22, respectively, was perfused with a mixture of 10 mL human plasma of blood group A and 10 mL NaCl-solution in a tempered hood at 37° C. for 2 h at a flow rate of 2.5 mL/h and a 40% filtration, followed by a dead-end filtration for further 2 h. Probes were taken from the resulting pool with which the determination of IgM antibody titer with a gel test assay from Bio-Rad Laboratories, see above, was carried out. Therefore, serial dilutions of the probes were prepared. 50 µL of plasma or plasma dilution, respectively, were mixed with 50 µL erythrocytes B in NaCl cards and were incubated 15 min at room temperature. In the next step, the probes were centrifuged in an ID-centrifuge (DiaMed AG) and the gel cards were evaluated with regard to agglutination.

Similarly, the IgG antibody titer was determined. First, serial dilutions of the probes were prepared. Then, 50 µL of plasma or plasma dilution, respectively, were mixed with 50 µL erythrocytes B in Coombs cards and were incubated 15 min at room temperature. In the next step, the probes were centrifuged in an ID-centrifuge (DiaMed AG) and the gel cards were evaluated with regard to agglutination.

The results are summarized in the following tables V and VI. The values in parentheses are the dead-end results.

TABLE V

| IgM Hollow fibers + ammonia plasma | | |
|---|---|---|
| | Start titer | End titer |
| AA + TsB_AP | 1:32 | 1:16 |
| AA + TsB_ANA | 1:32 | 1:4 |
| GMA + TsB_ANA | 1:32 | 1:16 (1:8) |

TABLE VI

| IgG Hollow fibers + ammonia plasma | | |
|---|---|---|
| | Start titer | End titer |
| AA + TsB_AP | 1:32 | 1:8 |
| AA + TsB_ANA | 1:32 | 1:2 |
| GMA + TsB_ANA | 1:32 | 1:16 (1:8) |

The invention claimed is:

1. A separation material of formula (VI) for selective separation of a blood group A determinant and/or a blood group B determinant from blood, blood plasma, or a blood product $$\text{matrix-N(H)-C(O)-R}^1\text{-[C(R}^a\text{)(H)]}_x\text{-K-L-R}^b_c\text{-F}^2_d\text{-M}^1\text{-(R}^2\text{-R}^3)_r\text{-R}^2\text{-W-saccharide} \quad (VI)$$

wherein
saccharide represents a blood group A determinant and/or a blood group B determinant;
$R^1$ represents, independently of one another, straight-chain or branched $C_1$-$C_{10}$ alkyl, wherein the alkyl group can be unsubstituted, or substituted with at least one substituent, selected from the group of substituents comprising halogen, alkyl, alkoxy, haloalkyl, cyano, nitro, amino, amidino, hydroxy, thiol, acylamino, alkoxycarbonylamino, haloalkoxycarbonylamino or alkylsulfonylamino;
$R^a$ represents —H, methyl or ethyl;
K represents —CO—, —NH— or —CH$_2$—;
L represents —CH$_2$—, —NH— or —O—;
$R^b$ represents, independently of one another, straight-chain or branched $C_1$-$C_{10}$ alkyl such as methyl, ethyl, n- or iso-propyl, n-, iso-, sec- or tert-butyl, n- pentyl, n-hexyl, n-heptyl, n-octyl, n-nonyl or n- decyl, wherein the alkyl group can be unsubstituted, or substituted with at least one suitable substituent, selected from the group of substituents consisting of halogen, alkyl, alkoxy, haloalkyl, cyano, nitro, amino, amidino, hydroxy, thiol, acylamino, alkoxycarbonylamino, haloalkoxycarbonylamino or alkylsulfonylamino;
$F^2$ represents —NH—, —CH$_2$—, —C(O)—, —N═, —O—, —CH═, —CH(OH)—or CH$_2$—CH(OH)—;
c and d independently of each other represent 0 or 1;
$M^1$ represents —NH—, —CH$_2$—, —C(O)—, —N═, —O— or —CH═;
$R^2$ represents, independently of one another, straight-chain or branched $C_1$-$C_{10}$ alkyl, wherein the alkyl group can be unsubstituted, or substituted with at least one suitable substituent, selected from the group of substituents consisting of halogen, alkyl, alkoxy, haloalkyl, cyano, nitro, amino, hydroxy, thiol, acylamino, alkoxycarbonylamino, haloalkoxycarbonylamino or alkylsulfonylamino;
$R^3$ represents, independently of each other, —CO—NH—, —NH—CO—, —CO—NH—NH—, —NH—NH—CO—, —CH═N—NH—, —NH—N═CH—, —N═CH—, —CH═N — or triazolyl,
r represents 0 or an integer from 1-10;
w represents —O—, —S—, —CH$_2$— or —NR'—, wherein R' represents H, or methyl;
x represents an integer from 1-50.

2. A method for producing a separation material according to claim 1, comprising
a) providing a matrix of the formula (I)

$$N^1\text{-matrix} \quad (I),$$

wherein
$N^1$ represents H$_2$N—, NH$_2$—NH — or epoxy;
b) providing a thermally labile radical initiator of the formula (II)

$$HO_2C—R^1—Y—R^1—CO_2H \quad (II),$$

wherein
Y represents —N═N— or —O—O—, and
$R^1$ represents, independently of one another, straight-chain or branched $C_1$-$C_{10}$ alkyl such as methyl, ethyl, n- or isopropyl, n-, iso- , sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents consisting of halogen, alkyl, alkoxy, haloalkyl, cyano, nitro, amino, amidino, hydroxy, thiol, acylamino, alkoxycarbonylamino, haloalkoxycarbonylamino or alkylsulfonylamino ;
c) providing at least one polymerizable monomer of formula (III)

$$H_2C═C(R^a)—K\text{-}L\text{-}R^b_c—F^1_d \quad (III)$$

wherein
$R^a$ represents —H, methyl or ethyl,
K represents —CO—, —NH— or —CH$_2$—,
L represents —H, —NH— or —O—,
$R^b$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents consisting of halogen, alkyl, alkoxy, haloalkyl, cyano, nitro, amino, amidino, hydroxy, thiol, acylamino, alkoxycarbonylamino, haloalkoxycarbonylamino or alkylsulfonylamino,
c and d represent, independently of one another, 0 or 1, and
$F^1$ represents —OH, —NH$_2$, —H, —N$_3$, —CO$_2$H, —CHO, —NH—NH$_2$, —C≡CH or epoxy;

d) providing at least one saccharide having the formula (V)

wherein

W represents O, S, $CH_2$ or NR', wherein R' represents H, methyl or a suitable amino protecting group, $R^2$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents consisting of halogen, alkyl, alkoxy, haloalkyl, cyano, nitro, amino, hydroxy, thiol, acylamino, alkoxycarbonylamino, haloalkoxycarbonylamino or alkylsulfonylamino, $R^3$ represents, independently of each other, —CO—NH—, —NH—CO—, —CO—NH—NH—, —NH—NH—CO—, —CH=N—NH—, —NH—N=CH—, —N=CH—, —CH=N— or triazolyl, M represents —COOH, —$NH_2$, —C≡C, —$N_3$, —NH—$NH_2$ or —OH, r represents 0 or an integer from 1-10;

e) coupling the matrix of formula (I) to the thermally labile radical initiator of formula (II), f) reacting the resulting matrix surface with a solution of the at least one polymerizable monomer of formula (III) under conditions which allow thermally initiated graft copolymerization and/or polymerization of the at least one monomer, wherein functional polymer chains are created on the surface of the matrix, and g) coupling the at least one saccharide of formula (V) to the functional polymer chains on the surface of the matrix.

3. The method of claim 2 further comprising providing a compound of formula (IV)

wherein $R^2$ is defined as in claim 1, $R^4$ independently of one another represents —O—, —S—, —CO—NH—, —NH—CO—, —N=CH— or —CH=N—, $R^{4A}$ represents HOOC—, $H_2N$—, C≡C, $N_3$—, $NH_2$—NH— or OH—, $E^1$ represents —COOH, —CHO, —$NH_2$, —SH, —OH, —$N_3$, —NH—$NH_2$ or —C≡C, n represents 0 or an integer from 1-600, and wherein in step (g) the compound of formula (IV) is first attached via its terminal functional group to the functional polymer chains on the matrix, and the resulting product is then coupled to the saccharide of formula (V).

4. The method according to claim 3 wherein $N^1$ represents $H_2N$— or epoxy,

Y represents —N=N—,

K represents —CO— or —NH—, $R^b$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents comprising halogen, alkyl, alkoxy, haloalkyl, cyano, nitro, amino, amidino, hydroxyl or thiol, c and d represent, independently of each other, 0 or 1, W represents O, S or NR', wherein R' represents H, methyl or a suitable amino protecting group, $R^3$ independently of one another represents —CO—NH—, —NH—CO—, —CO—NH—NH—, —NH—NH—CO—, —N=CH— or —CH=N—, and M represents —COOH, —$NH_2$, —C≡C, —$N_3$ or —NH—$NH_2$.

5. The method according to claim 3 wherein $R^2$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents comprising halogen, alkyl, alkoxy, haloalkyl, cyano, nitro, amino, hydroxyl or thiol, $R^4$ independently of one another represents —O—, —CO—NH—, —NH—CO—, —N=CH— or —CH=N—, $R^{4A}$ represents HOOC—, $H_2N$—, C≡C—, $N_3$— or $NH_2$—NH—, and E1 represents —COOH, —CHO, —$NH_2$, —$N_3$, —NH—$NH_2$ or —C≡C.

6. The method according to claim 2 wherein $N^1$ represents $H_2N$— or epoxy,

Y represents —N=N—,

K represents —CO— or —NH—, $R^b$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents comprising halogen, alkyl, alkoxy, haloalkyl, cyano, nitro, amino, amidino, hydroxyl or thiol, c and d represent, independently of each other, 0 or 1, W represents O, S or NR' wherein R' represents H, methyl or a suitable amino protecting group, $R^3$ independently of one another represents —CO—NH—, —NH—CO—, —CO—NH—NH—, —NH—NH—CO—, —N=CH— or —CH=N—, and M represents —COOH, —$NH_2$, —C≡C, —$N_3$ or —NH—$NH_2$.

7. The method according to claim 6 wherein $R^2$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents comprising halogen, alkyl, alkoxy, haloalkyl, cyano, nitro, amino, hydroxyl or thiol, $R^4$ independently of one another represents —O—, —CO—NH—, —NH—CO—, —N=CH— or —CH=N—, $R^{4A}$ represents HOOC—, $H_2N$—, C≡C—, $N_3$— or $NH_2$—NH—, and E1 represents —COOH, —CHO, —$NH_2$, —$N_3$, —NH—$NH_2$ or —C≡C.

8. The method according to claim 2 wherein $R^2$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, wherein the alkyl group can be unsubstituted, or substituted with at least one suitable substituent, selected from the group of substituents comprising halogen, alkyl, alkoxy, haloalkyl, cyano, nitro, amino, hydroxyl or thiol, $R^4$ independently of one another represents —O—, —CO—NH—, —NH—CO—, —N═CH— or —CH═N—, $R^{4.4}$ represents HOOC—, $H_2N$—, C≡C—, $N_3$— or $NH_2$—NH—, and $E^1$ represents —COOH, —CHO, —$NH_2$, —$N_3$, —NH—$NH_2$ or —C≡C.

9. The method of claim 2 wherein $F^1$ represents epoxy.

10. The method of claim 2 wherein x is greater than one.

11. The separation material according to claim 1 wherein the matrix is a synthetic polymer, a peptide or a polysaccharide.

12. The separation material according to claim 11, wherein the matrix is prepared from hydrophilic and/or hydrophobic synthetic polymers selected from the group consisting of polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate, poly (methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly (p-phenylene ether) (PPE), polyurethane (PU), styrene acrylonitrile (SAN), polybutenoic acid, poly (4-allyl-benzoic acid), poly (glycidyl acrylate), polyglycidyl methacrylate (PGMA), poly(allyl glycidyl ether), poly (vinyl glycidyl ether), poly (vinyl glycidyl urethane), polyallylamine, polyvinylamine and copolymers thereof.

13. The separation material according to claim 11, wherein the matrix is prepared from hydrophilic and/or hydrophobic synthetic polymers selected from the group consisting of polyacrylates (PA), poly (methyl methacrylate) (PMMA) or polyglycidyl methacrylate (PGMA), polyvinylpyrrolidone (PVP), polysulfone (PS), polyethersulfone (PES), polyarylethersulfone (PAES) and combinations thereof.

14. The separation material according to claim 11 wherein the matrix has the form of beads, flat sheet membrane or hollow fiber membrane.

15. The separation material according to claim 14, wherein the flat sheet or hollow fiber membrane is treated with gas plasma before coupling a thermally labile radical initiator.

16. A device for separating, from a liquid, substances with an affinity to a saccharide, comprising a separation material according to claim 1.

17. A method for preparing a separation material according to claim 1 comprising a) providing a matrix of the formula (I)

$$N^1\text{-matrix} \qquad (I),$$

b) providing a thermally labile radical initiator of the formula (II)

$$HO_2C\text{—}R^1\text{—}Y\text{—}R^1\text{—}CO_2H \qquad (II),$$

c) providing a polymerizable monomer of formula (III)

$$H_2C\text{=}C(R^a)\text{—}K\text{-}L\text{-}R^b_c\text{—}F^1_d \qquad (III)$$

d) providing a saccharide having the formula (V)

$$\text{saccharide-}W\text{—}R^2\text{—}(R^3\text{—}R^2)_r\text{-}M \qquad (V),$$

e) coupling the matrix to the thermally labile radical initiator, f) reacting the resulting matrix surface with a solution of the polymerizable monomer of formula (III) under conditions which allow thermally initiated graft copolymerization of the monomer, wherein functional polymer chains are created on the surface of the matrix, and g) coupling the saccharide to the functional polymer chains on the surface of the matrix.

18. A method according to claim 17 for preparing a separation material according to claim 1 further comprising providing a compound of formula (IV), $$R^{4.4}\text{—}R^2\text{—}(R^4\text{—}R^2)_n\text{-}E^1 \qquad (IV)$$

and wherein (g) coupling the saccharide to the functional polymer chains on the surface of the matrix comprises first attaching the compound of formula (IV) via its terminal functional group to the functional polymer chains on the matrix, and then coupling the resulting product to the saccharide of formula (V).

19. The separation material of claim 1 wherein x is greater than one.

* * * * *